(12) United States Patent
Donohue et al.

(10) Patent No.: US 10,670,543 B2
(45) Date of Patent: Jun. 2, 2020

(54) SYSTEM AND METHOD FOR MONITORING ENVIRONMENTAL STATUS THROUGH REACTIVE REFLECTORS

(71) Applicant: Azila Holdings, LLC, Roseville, CA (US)

(72) Inventors: Brenna Elizabeth Donohue, Roseville, CA (US); Patrick Francis Donohue, Roseville, CA (US)

(*) Notice: Subject to any disclaimer, the term of this patent is extended or adjusted under 35 U.S.C. 154(b) by 125 days.

(21) Appl. No.: 16/046,745

(22) Filed: Jul. 26, 2018

(65) Prior Publication Data
US 2018/0356351 A1    Dec. 13, 2018

Related U.S. Application Data

(63) Continuation of application No. 15/213,000, filed on Jul. 18, 2016, now Pat. No. 10,060,863.
(Continued)

(51) Int. Cl.
*G01N 27/10*  (2006.01)
*G01N 27/12*  (2006.01)
(Continued)

(52) U.S. Cl.
CPC ............ *G01N 22/04* (2013.01); *G01N 27/10* (2013.01); *G01N 27/12* (2013.01); *G01N 27/002* (2013.01);
(Continued)

(58) Field of Classification Search
CPC ...... G01N 22/04; G01N 27/002; G01N 27/10; G01N 27/12; G01N 27/126; G01N 27/60; G01N 33/0031
See application file for complete search history.

(56) References Cited

U.S. PATENT DOCUMENTS

| 4,596,697 A | 6/1986 | Ballato |
| 6,677,859 B1 | 1/2004 | Bensen |

(Continued)

FOREIGN PATENT DOCUMENTS

| CN | 104899617 A | 9/2015 |
| EP | 1542635 B1 | 4/2012 |
| KR | 20100063470 A | 6/2010 |

OTHER PUBLICATIONS

"Without a Trace", Los Alamos National Laboratory, Mar. 8, 2016, www.lanl.gov/discover/publications/1663/2016-march/without-trace.php, Dept of Energy NNSA, Los Alamos, USA.
(Continued)

*Primary Examiner* — Jennifer Wecker
(74) *Attorney, Agent, or Firm* — Alpine Patents LLC; Brian Van Osdol

(57) ABSTRACT

A system and method for monitoring environmental state that includes a structure element with a base substrate and at least one reflector element integrated to the base substrate, wherein the reflector element is physically configured with at least one response signature that is discretely expressed based on an substance induced environmental condition of the reflector element; and a remote monitor device comprising a transmitter and receiver unit and a controller, wherein the monitor device is configured to interrogate the structure element; detect a response signature corresponding to at least the one reflector element; and map the response signature to a corresponding substance induced environmental condition.

20 Claims, 21 Drawing Sheets

Related U.S. Application Data

(60) Provisional application No. 62/194,152, filed on Jul. 17, 2015, provisional application No. 62/305,416, filed on Mar. 8, 2016.

(51) Int. Cl.
　　　*G01N 22/00*　　　(2006.01)
　　　*G01N 22/04*　　　(2006.01)
　　　*G01N 33/00*　　　(2006.01)
　　　*G01N 27/60*　　　(2006.01)
　　　*G01N 27/00*　　　(2006.01)

(52) U.S. Cl.
　　　CPC ........... *G01N 27/126* (2013.01); *G01N 27/60* (2013.01); *G01N 33/0031* (2013.01)

(56) References Cited

U.S. PATENT DOCUMENTS

| | | | |
|---|---|---|---|
| 8,697,485 | B2 | 4/2014 | Crain et al. |
| 8,736,425 | B2 * | 5/2014 | Potyrailo ............... G01D 21/00 324/655 |
| 2009/0009332 | A1 * | 1/2009 | Nunez .................. A01K 11/007 340/572.1 |
| 2009/0057415 | A1 | 3/2009 | Partanen et al. |
| 2011/0057791 | A1 | 3/2011 | Durgin et al. |
| 2013/0015248 | A1 | 1/2013 | Perret et al. |
| 2015/0177114 | A1 | 6/2015 | Kapoor et al. |
| 2017/0016838 | A1 | 1/2017 | Donohue et al. |

OTHER PUBLICATIONS

Arnaud Vena, "Chipless RFID Tag Using Hybrid Coding Technique", IEEE Transactions on Microwave and Techniques, vol. 59, No. 12, Dec. 2011 (3356-3364).

Bryce Kellogg, "Passive Wi-Fi: Bringing Low Power to WiFi Transmissions", University of Washington, http://passivewifi.cs.washington.edu/files/passive_wifi.pdf.

Claire Swedberg, "Murata Mass-Produces 'World's Smallest HF Tag'", RFID Journal, Oct. 11, 2012, "http://www.rfidjournal.com/articles/view?10017".

Gady Konvalina, "Sensors for Breath Testing: From Nanomaterials to Comprehensive Disease Detection", Accounts of Chemical Research, Research Gate, The Department of Chemical Engineering and Russell Berrie Nanotechnology Institute, Technion—Isreal Institute of Technology, Haifa 3200003, Israel.

Joshua F. Ensworth, "Every Smart Phone is a Backscatter Reader: Modulated Backscatter Compatibility with Bluetooth 4.0 Low Energy (BLE) Devices", 2015 IEEE International Conference on RFID (RFID), (78-85).

Laura K. Wood, "Paper Substrates and Inks for Printed Electronics", Department of Paper Engineering and Imaging, Department of Material Science and Engineering, Western Michigan University, Kalamazoo, MI, Center for Coating Development, Center for Ink and Printability Research.

Louisa Dalton, "Bendable Breath Sensor Detects Ovarian Cancer", Chemical & Engineering News, American Chemical Society, https://cen.acs.org/articles/93/web/2015/09/Bendable-Breath-Sensor-Detects-Ovarian.html, Sep. 22, 2015.

M. Dragoman, "Graphene Radio: Detecting Radiowaves with a Single Atom Sheet", National Institute for Research and Development in Microtechnology (IMT) Bucharest, Romania. (1-11).

Mingquan Yuan, "Self-Powered Wireless Affinity-Based Biosensor Based on Integration of Paper-Based Microfluidics and Self-Assembled RFID Antennas", IEEE Transactions on Biomedical Circuits and Systems, May 2016.

Munawar Hussain, "Biomimetic Strategies for Sensing Biological Species", Biosensors Mar. 2013, (89-107), www.mdpi.com/journal/biosensors/, Department of Analytical Chemistry, University of Vienna, Waehringer Strasse 38, A-100-90, Vienna, Austria. MDPI, Basel, Switzerland.

Petri Ihalainen, Application of Paper-Supported Printed Gold Electrodes for Impedimetric Immunosensor Development, Biosensors 2013, 3, 1-17; doi:10.3390/bios3010001, www.mdpi.com/journal/biosensors/.

Rob Matheson, "Wireless, wearable toxic-gas detector", MIT News Office, Jun. 30, 2016.

Robert Blue, "Miniature nitro and peroxide vapor sensors using nanoporous thin films", IEEE Sensors Journal, DOI 10,1109/JSEN.2016.2559442.

Smail Tedjini, "Hold the Chips", IEEE microwave magazine, Jul./Aug. 2013, Digital Object Identifier 10.1109/MMM.2013.2259393, Jul. 11, 2013.

Suguna Perumal, "A Study of Adhesion Forces between Vinyl Monomers and Graphene Surfaces for Non-covalent Functionalization of Graphene", Carbon (2016), doi: 10.1016/j.carbon.2016.05.049., May 22, 2016.

Thomas Chretiennot, A Microwave and Microfluidic Planar Resonator for Efficient and Accurate Complex Permittivity Characterization of Aqueous Solutions, IEEE Transactions on Microwave Theory and Techniques, https://login.appcoll.com/RefDetails.aspx?groupid=512&plid=128315, vol. 61 Issue 2, pp. 972-978.

Yaacov Michlin, "Yissum Showcases Hebrew University's Breakthroughs in Advanced Materials Technologies", Yissum Research Development Company of the Hebrew University of Jerusalam, Mar. 21, 2016, Jerusalem, Isreal.

Yahiea Al-Naiemy, "A Systematic Approach for the Design, Fabrication, and Testing of Microstrip Antennas Using Inkjet Printing Technology", ISRN Communications and Networking, vol. 2012, Article ID 132465, 11 pages, doi:10.5402/2012/132465.

* cited by examiner

Configured
Response Sig: X1

Configured
Response Sig: X2

SYSTEM AND METHOD FOR MONITORING ENVIRONMENTAL STATUS THROUGH REACTIVE REFLECTORS

CROSS-REFERENCE TO RELATED APPLICATIONS

This Application is a continuation application of U.S. patent application Ser. No. 15/213,000, filed on Jul. 18, 2016, which claims the benefit of U.S. Provisional Application No. 62/194,152, filed on Jul. 17, 2015 and of U.S. Provisional Application No. 62/305,416, filed on Mar. 8, 2016, both of which are incorporated in their entireties by this reference.

TECHNICAL FIELD

This invention relates generally to the field of remote environmental sensing, and more specifically to a new and useful system and method for monitoring environmental status through reactive reflectors.

BACKGROUND

There are numerous products that address fluid absorption issues in the personal health and medical space. Feminine hygiene products (e.g., a tampon sanitary pads), baby and senior diapers, bandages, hemostatic devices, and/or products that address similar issues of absorbing a fluid. Such products also suffer from similar problems and challenges relating to unpredictability of state of the fluid absorption of the product. This can result in leaks and user discomfort in some cases, and it can lead to premature removal of the product in other cases. Similarly, there are numerous alternative scenarios where it may be beneficial to monitor the environmental conditions at one or more points. To perform such monitoring, active sensors are often employed in locations where the environment is monitored. However, electrical sensors require power and processing power. This can make sensing solutions impractical from a cost and technical complexity standpoint. Thus, there is a need in the remote environmental sensing field to create a new and useful system and method for monitoring environmental status through reactive reflectors. This invention provides such a new and useful system and method.

DESCRIPTION OF THE EMBODIMENTS

The following description of the embodiments of the invention is not intended to limit the invention to these embodiments but rather to enable a person skilled in the art to make and use this invention.

1. System for Reactive Reflectors

Figure 1:
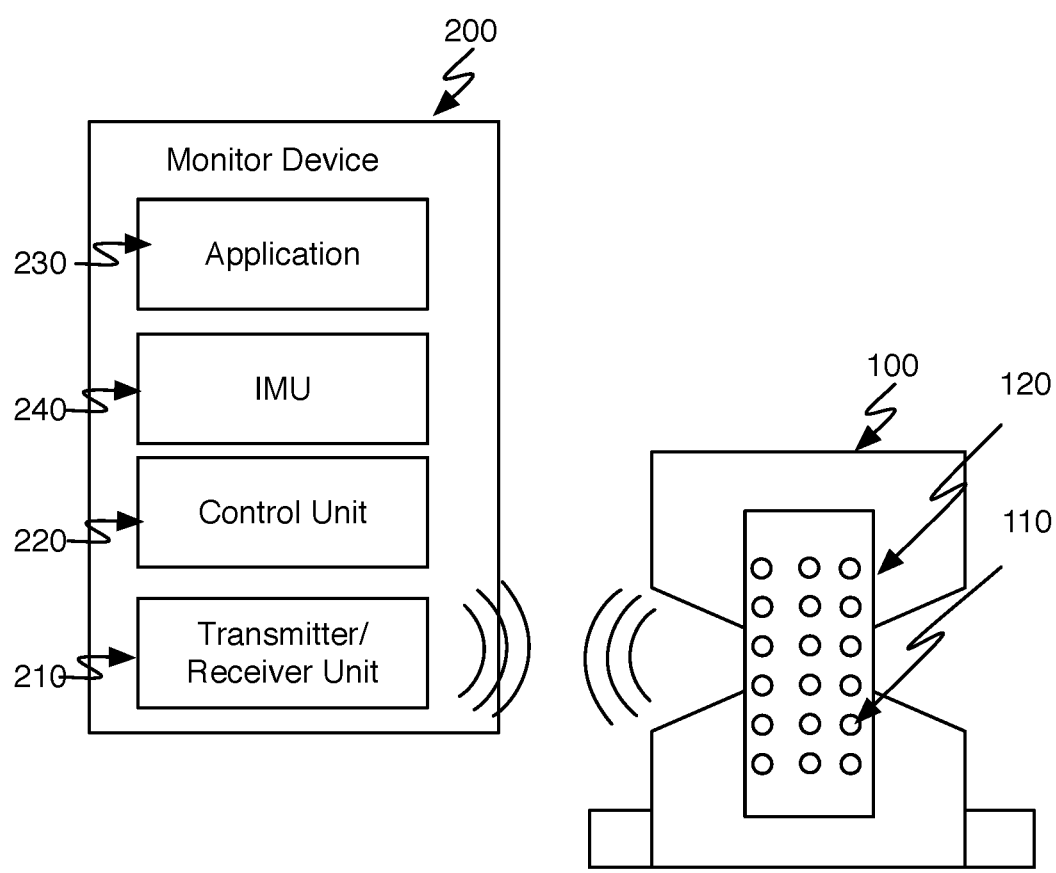
FIG. 1 is a schematic representation of a system of a preferred embodiment.

As shown in FIG. 1, a system for monitoring environmental status through reactive reflectors of a preferred embodiment can include a first structure element 100 with at least one integrated reflector element 110 on a base substrate 120 and a remote monitor device 200 that includes a transmitter and receiver unit 210 and a control unit 220. The system and method function to enable monitoring of environmental conditions of a structure element 100 based on the at least one integrated reflector element 110. A reflector element 110 is preferably integrated into the base substrate 120, and more preferably, the reflector element 110 is printed using conductive ink on the base substrate 120. In some variations, a set of reflector elements 110 are integrated at various positions within the structure element 100. A reflector element 110 is preferably physically configured with at least one response signature that is expressed at least partially based on an environmental substance condition of the structure element 100. A reflector element 110 preferably includes an antenna structure 112 printed on the base substrate using conductive ink, wherein the antenna structure is configured with an electromagnetic resonance frequency that corresponds to the response signature of the reflector element.

The response signature is preferably used with the system as an identifier expressed during interrogation depending on the environmental condition. The presence of a response signature can act as an identifier that is dependent on the conditions at that reflector. For example, the response signature may be expressed if the environmental condition has not yet been satisfied at the location of the reflector element 110, if the environmental condition has previously been satisfied at the location of the reflector element 110, and/or based on the current environmental condition depending on the configuration of the reflector element 110. A monitor device 200 preferably interrogates a space where a reflector element 110 may be present. An assessment of the environmental state can be generated at the monitor device 200 based on presence or lack of a detected response signature.

The system is preferably used to translate changes in an environment to a change in electromagnetic or magnetic energy detected at a monitor device. A reflector element 110 and optionally other optional components at the site of the reflector element 110 facilitate the translation of environmental conditions into how electromagnetic or magnetic energy is reflected or transmitted from the reflector element 110. Accordingly, the system can operate according to an environment variable, a reflector element variable, electromagnetic or magnetic energy variable (e.g., when transmitting or receiving), and/or an optional reactive component variable. The reactive component is preferably a secondary reactive layer (e.g., such as a chemically reactive polymer), which acts as an intermediary between the environment and a reflector element 110 with the purpose of altering the response of the reflector thus sending a message about a substance in the environment.

As a first potential benefit, the system can enable efficient and cheaply produced mechanisms for detecting environmental status so that various conditions can be detected or sensed at various points within a structure element 100. Some implementations of reflector elements 110 do not utilize any active electronics, integrated circuitry other than an antenna structure 112. Reflector elements could be affordably printed on objects that may even be disposable.

As another potential benefit, the system can be applied to a variety of detection scenarios. The system can be applied to various forms of environmental condition detection such as liquid or fluid saturation-level detection, chemical-presence detection, chemical exposure level detection, physical disruption of the structure element, or other forms of environmental condition detection. The environmental condition is preferably a substance induced environmental condition wherein the environmental condition can be used to determine the state of a substance within the environment. A substance induced environmental condition can be used to determine the presence or lack or a presence of a substance relative to defined quantity threshold, the amount of a substance, the mixture of multiple substances, how much of a substance has been absorbed at a site of a reflector element 110, and/or any suitable environmental condition.

As another potential benefit, the system can utilize multiple reflector elements 110 to generate time and location based analysis of conditions. For example, the system can be used to predict full saturation of an absorbent pad, to indicate the fluid level of a container, or mark the vector of an airborne chemical.

The system may have particular application to monitoring and predicting changes of fluid presence in an absorbent device. In one dryness-monitoring embodiment, the system uses electromagnetic and/or magnetic signal of the monitor device to monitor the dryness state of the reflector elements 110 in the structure element 100. The reflector elements 110 are preferably arranged in a predetermined pattern so by monitoring each reflector element 110 the dryness state of the structure element 100 can be determined. The dryness state can include various forms of information such as: fluid absorbance, fluid flow prediction (e.g., when it will be time to change structure element 100 for new, prior to failure to contain) fluid origin, fluid quantification, border of remaining dry area, product life prediction, percentage remaining dry and rate of change, and/or any suitable information.

In one variation, a subset of identifiable reflector elements 110 can be chemically or environmentally reactive so as to provide alternative or additional monitoring capabilities. The response signature can be discretely expressed based on a chemical reaction between a material of the structure element (e.g., a reflector element 110, a base substrate 120, and/or a secondary reactive layer 130) and a targeted substance contacted within the environment. The chemical reaction could be a biochemical reaction to detect biological signals, a chemical reaction to detect airborne chemicals, or any suitable type of chemical reaction. For example a reactive coating encasing the reflector elements 110 can alter the signal response of the antennas when exposed to particular substances, molecules, atoms, and/or conditions. For example, a biochemical reagent could be used to alter the response signature of a reflector based on the detected biochemistry of a subject (e.g., a human).

In one preferred application of the system, the structure element 100 is an absorption device enhanced with dryness monitoring such as a feminine hygiene product (e.g., a tampon or sanitary pad), a diaper, a bandage, a hemostatic device, or any suitable absorbent product. The system can be a monitoring and alerting system. In the personal health product space, the system can function to monitor and alert one or more users of fluid absorbance, leaking, fluid/bleeding source, bleeding/fluid quantification, and/or fluid distribution. Monitoring and alerting may prevent accidents, soiling of clothing, and corresponding discomfort for a subject. In the institutional space, monitoring and alerting may additionally reduce the occurrence of pressure sores for the bed ridden by keeping track of such factors as indications of epidermal cellular damage, the patient's time in one position, compliance with doctors orders regarding activity, and alerting staff and physicians of an impending risk while also interfacing with automated charting. Also, it may prevent the occurrence of prematurely changing a personal health product such as a bandage or cast, which can reduce waste.

Figure 2:
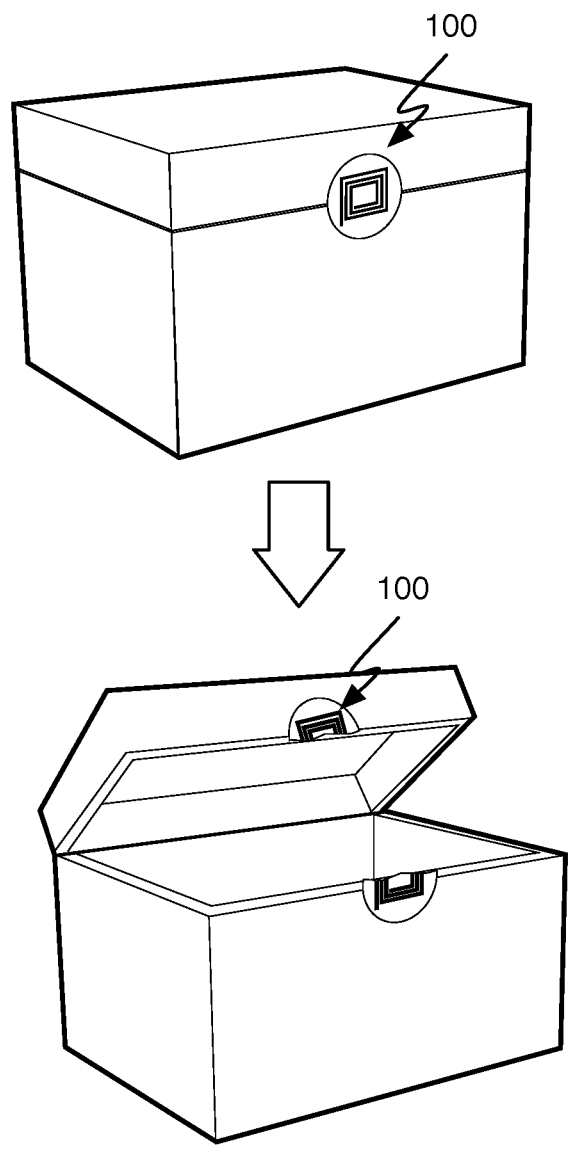
FIG. 2 is a schematic representation of a structure element of a seal-based embodiment.
Figure 3:
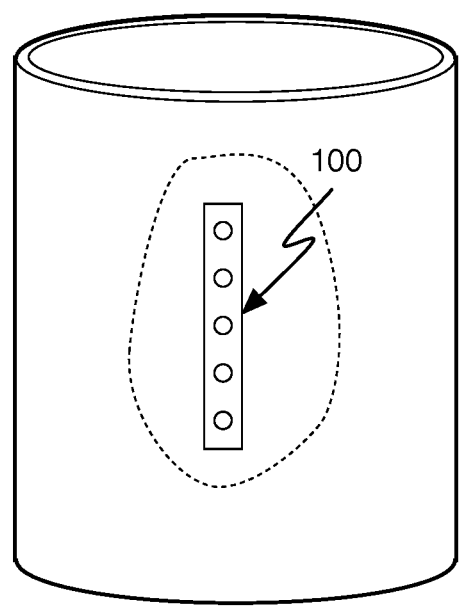
FIG. 3 is a schematic representation of a structure element used in a container monitoring embodiment.

The system can alternatively or additionally be applied to areas outside of the health space such as sealing applications, fluid transportation, or any industrial application of locally or remotely detecting the leaking or draining of a fluid or other substances that may alter the signal response of the reflector elements 110. For example, a seal made of one or more reflector elements 110 can have a unique response signature destructively prevented if the seal is broken as shown in FIG. 2. This could be remotely detected, triggering an appropriate alert. In another example, a set of reflector elements can line the length of an internal wall of a container as shown in FIG. 3. The level of a substance in the container could be detected based on the response of the reflector elements 130 to contact with the substance.

In a preferred implementation, a user will employ a personal computing device such as a smart phone, smart watch, smart ring or other computing device used for general computing purposes in addition to interacting and monitoring the status of an absorption device. As an exemplary use-case, a woman would buy a package of sanitary pads enhanced with reflector elements 110. She then can use the monitor device application on her phone to initialize remote monitoring of the enhanced sanitary napkin. By placing the phone in her pocket or reasonably nearby, the monitor device application can periodically scan the absorption device. The electromagnetic and/or magnetic signal response of the reflector elements 110 in the absorption device can then be used to determine the overall state of the absorption device. Various notifications can be delivered to the woman including when menstruation begins, an estimate on when the absorption device should be changed, when leaking has occurred, and other suitable information.

The structure element 100 functions as chassis on which environmental condition monitoring is performed. The structure element 100 could be any suitable object. Reflector elements 110 can be positioned along the surface of the structure element 100. Reflector elements 110 may alternatively be integrated within the structure element 100. The structure element 100 could be any suitable object such as an absorbent device, a container, a seal, or any suitable object. In some variations, a set of reflector elements 110 are distributed across a set of different structure elements 100. In another variation, the structure element 100 can facilitate coupling of the reflector element 110 to a target object. For example, within a factory, structure element 100 could be a sticker that can be placed at various locations and objects.

In the variation, where the structure element 100 is an absorbent device, the structure element 100 can supply an auxiliary function of absorbing a fluid. Diapers, tampons, feminine hygiene pads and other form factors can provide absorption functionality. Absorption devices can be used in absorbing blood or other bodily fluids. Bandages or wraps may supply binding, compression, of other forms of physical support. The structure may include adhesive, rigid or semi-rigid structural components, and/or any suitable parts, which may contribute to the auxiliary functions of the structure element 100.

The structure element 100 can include one or more integrated reflector elements 110. The integrated identifiable reflector elements 110 are preferably conductive antenna patterns printed onto an internal or external surface of the structure element 100. The structure element 100 can act as the base substrate 120. Alternatively, a base substrate 120 can be an intermediary layer that can be attached to the structure element 100.

A reflector element 110 functions to supply an identifiable electromagnetic and/or magnetic signal response to inspection by the transmitter and receiver unit 210. The identifiable signal response is preferably dependent on the state of environmental conditions at the reflector element.

Figure 4A:
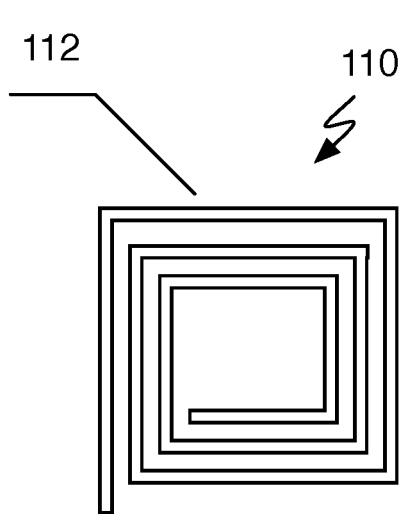
FIGS. 4A and 4B are two exemplary reflector elements with identifying response signatures.
Figure 4B:
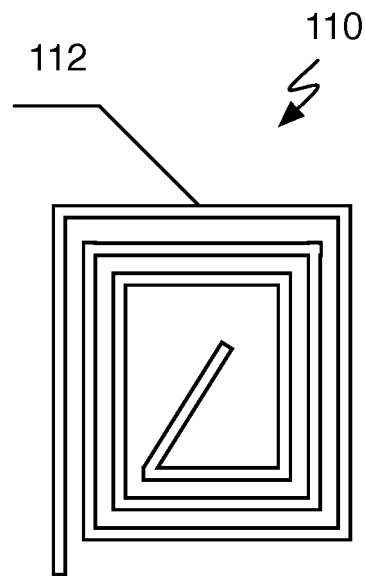
Figure 5:
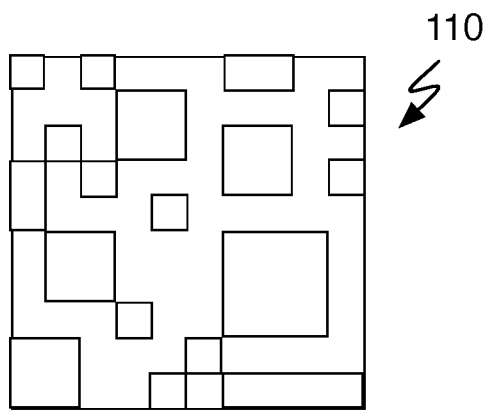
FIG. 5 is an exemplary representation of a patterned reflector element.

The reflector element 110 is preferably a passive radio frequency identifier that supplies an electromagnetic frequency response to an interrogation signal generated by the transmitter and receiver unit 210. The transmitter and receiver unit 210 preferably transmits an electromagnetic and/or magnetic signal and then evaluates the response. The response can be analyzed to detect the presence of a response signature used as an identifier of a reflector element 110. In one variation, a reflector element 110 can include an inductive antenna structure 112 pattern with a targeted resonance frequency. An antenna structure 120 may be a conductive path (e.g., a spiral) configured for a particular frequency response. Varying the conductive path can customize the frequency response such that two reflector elements 110 can be uniquely identified and distinguished as shown in FIGS. 4A and 4B. In one variation, the identifier of the reflector element 110 is associated with the resonance harmonic frequency of the reflector element 110. In another variation, the identifier of the reflector element 110 is a broadcasted identifier code configured for each particular reflector element 110 in the variation where the reflector element transmits the identifier code using induced electricity. When the transmitter and receiver unit 210 transmits an electromagnetic or magnetic signal at the resonance frequency of the reflector element 110, the reflector element 110 absorbs more of the electromagnetic frequency resulting in a change in the received signal strength at the transmitter and receiver unit 210. The transmitter receiver unit can process the backscatter of the transmission signal to detect patterns indicating the presence of the reflector element 110. In another alternative, the reflector element 110 can include circuit elements to provide a transmitted response. In the transmitted signal response variation, a signal transmitted by the transmitter and receiver unit 210 supplies sufficient energy such that the reflector element 110 can transmit a response signal back to the transmitter and receiver unit 210. That transmitted response from the reflector element 110 can be made conditional by having the antenna be enabled or disabled in response to environmental conditions. The signal response preferably includes identifying information.

Figure 19:
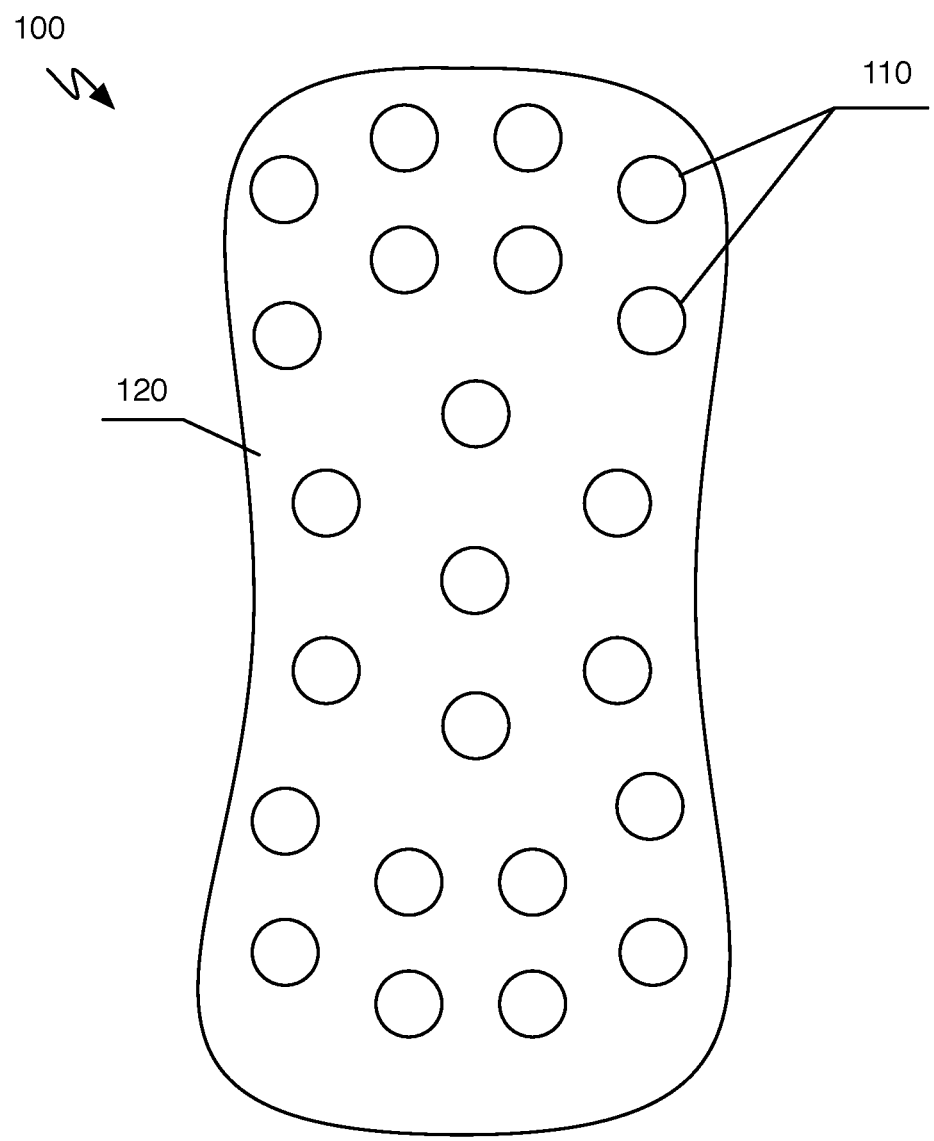
FIG. 19 is a schematic representation of an exemplary arrangement of reflector elements in a custom pattern.

In another variation, the reflector element 110 could be printed conductive pattern of one or multiple materials as shown in FIG. 19 that provides some detectable and identifiable response to interrogation. Interrogation of the conductive pattern will preferably have some discernible backscatter characteristics. For simplicity, herein, the reflector element 110 is described primarily as utilizing an antenna structure 112 but any suitable structure with an identifying interrogation response may be used.

In the preferred implementation of a reflector element 110, an antenna structure 112 is printed using conductive ink. The conductive ink may be any suitable type of printable conductive ink. In one variation, the conductive ink may be comprised of any noble metal(s) or alloy thereof, graphene, alterations or modifications thereof, 2D allotropes of graphene, alterations or modifications thereof, polymer(s) or any suitable conductive nanotubes, fine crystalline flakes or particles in a solvent or suitable vehicle or medium, and/or any suitable printable substance. The printed reflector elements 110 are preferably configured with a physical structure of an inductive loop, coil, fractal, or other suitable 2D or 3D patterns that have a targeted resonance frequency. The reflector elements 110 may alternatively be manufactured or produced with any suitable method. In one variation, the reflector elements 110 are manufactured separately from the structure unit and then mechanically coupled to the structure element 100 such as through adhesive or a fastening mechanism. The printing process can include any suitable pre or post manufacturing steps.

The structure element 100 is preferably reactive to some environmental condition. An environmental condition is preferably based on substance contact with a reflector element 110 such as contact with a gas, fluid, and/or a chemical. At least one component of the structure element 100 is altered during the environmental condition so as to transition or perturb the response signal of the reflector element 110. The identifying response signal is preferably altered in a discrete manner. Wherein discrete describes the expression of a response signature that is detectable or not detectable based on the environmental condition.

The reactive component can be the base substrate 120, the reflector element 110, and/or a secondary reactive layer 130 that is integrated with the reflector element 110. The reactive component could be made to change material properties to alter the response signature. For example, the impedance of a material could change in response to contact with a trigger substance. In one variation, by managing the atomic structure of a reactive component (e.g., a reflector element 110, a polymer coating, a substrate layer, etc.), one can tweak how it reacts to its immediate environment. Therefore, one can customize the atomic structure to enhance its reaction to specific electromagnetic stimulation and/or tune the surface to be ideal for interaction with certain substances which when encountered will bond with the surface thus altering the way the reflector responds to electromagnetic stimulation and thus the resulting backscatter or lack thereof. Additionally, one can adjust the surface of the reflector to enhance its relationship with the chemically reactive polymer thus enhancing how they perform together facilitating further expansion of capabilities.

The reactive component may alternatively be made to destructively perturb the reflector element 110. For example, parts of the reflector element 110 may be eroded, dissolved, or otherwise removed after a reaction with the reactive component.

Figure 6:
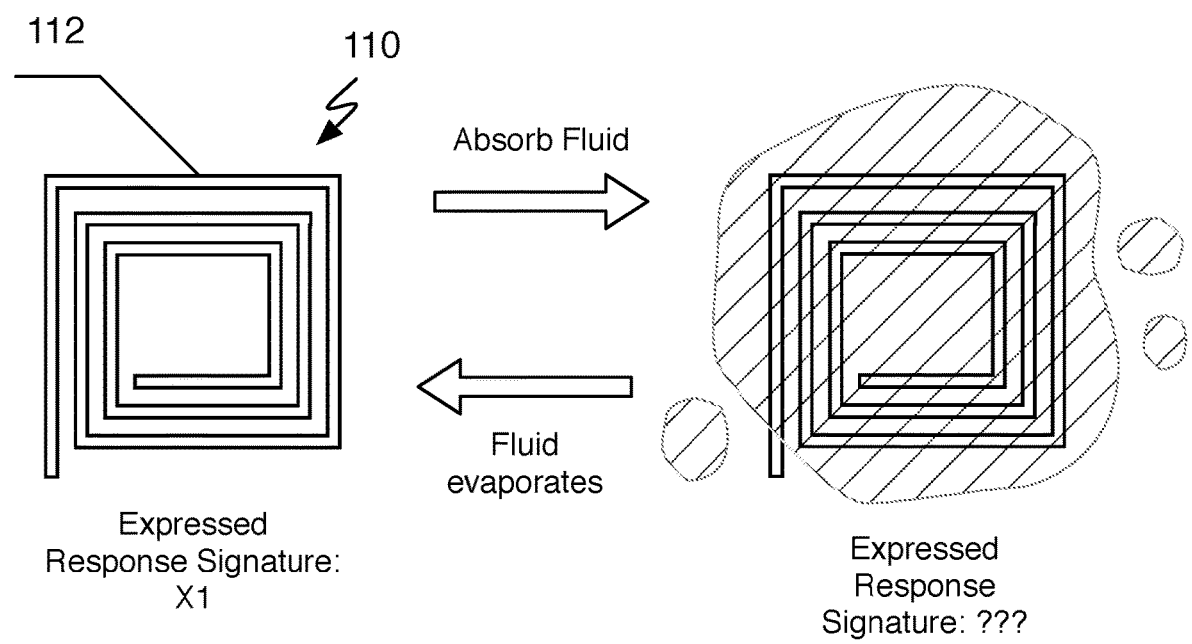
FIG. 6 is a schematic representation of toggle transitions between response signature states of a reflector element.

A reactive base substrate 120 could alter its interrogation response to interfere with the response signature of the antenna structure 112. For example, in the fluid detection scenario, fluid may be absorbed into the base-substrate 120. The amount of absorbed fluid can dampen the strength of a response signature of the reflector element 110 or block the response signature entirely as shown in FIG. 6.

Figure 7:
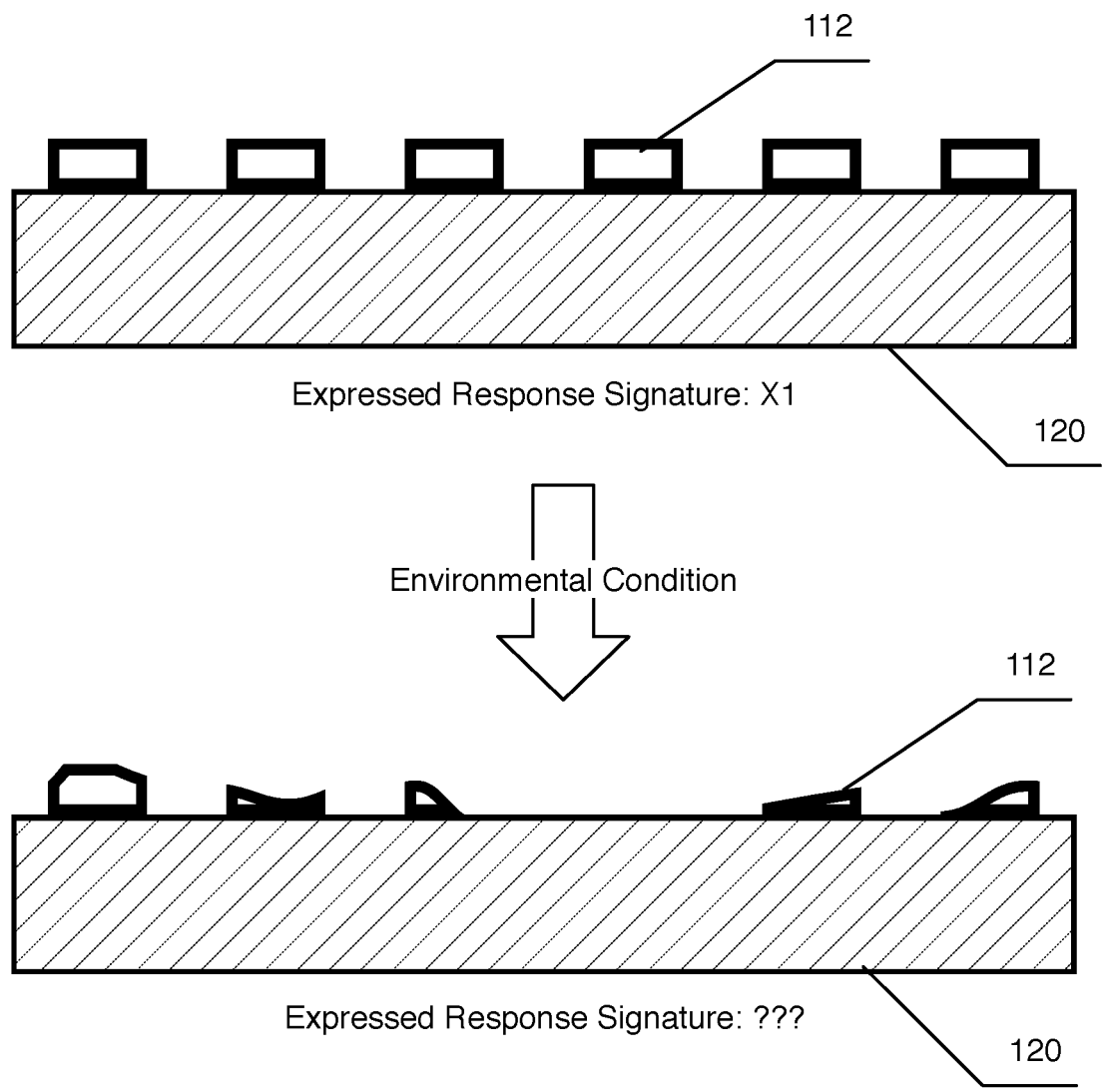
FIG. 7 is a schematic representation of a transition between response signature states of a deactivating reflector element with a reactive antenna structure.

A reactive reflector element 110 may include parts that are reactive to the environmental conditions. In one variation, an antenna coil may be made of a reactive substance reactive to a trigger substance. When the antenna coil makes contact with the trigger substance, the reactive substance may alter it's properties or change its physical structure. In a first example, the impedance of the reactive substance changes during the environmental condition. This impedance change may activate an antenna structure, wherein the antenna structure begins eliciting the response signature. In a second example, the reactive substance erodes when put in contact with the trigger substance. A conductive antenna structure may be eroded such that the antenna structure can no longer generate an initial response signature as shown in the cross sectional view of FIG. 7.

Figure 8:
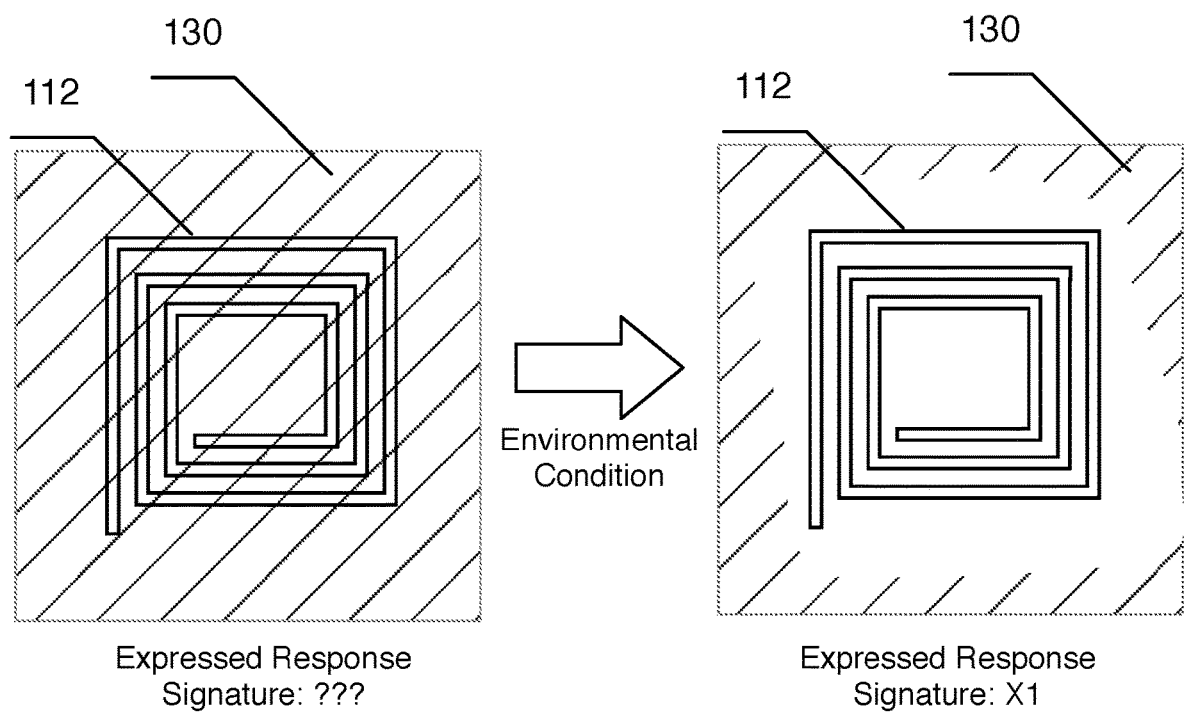
FIGS. 8 and 9 are schematic representations of a transition between response signature states of an activating reflector element with shielding reactive layer.
Figure 9:
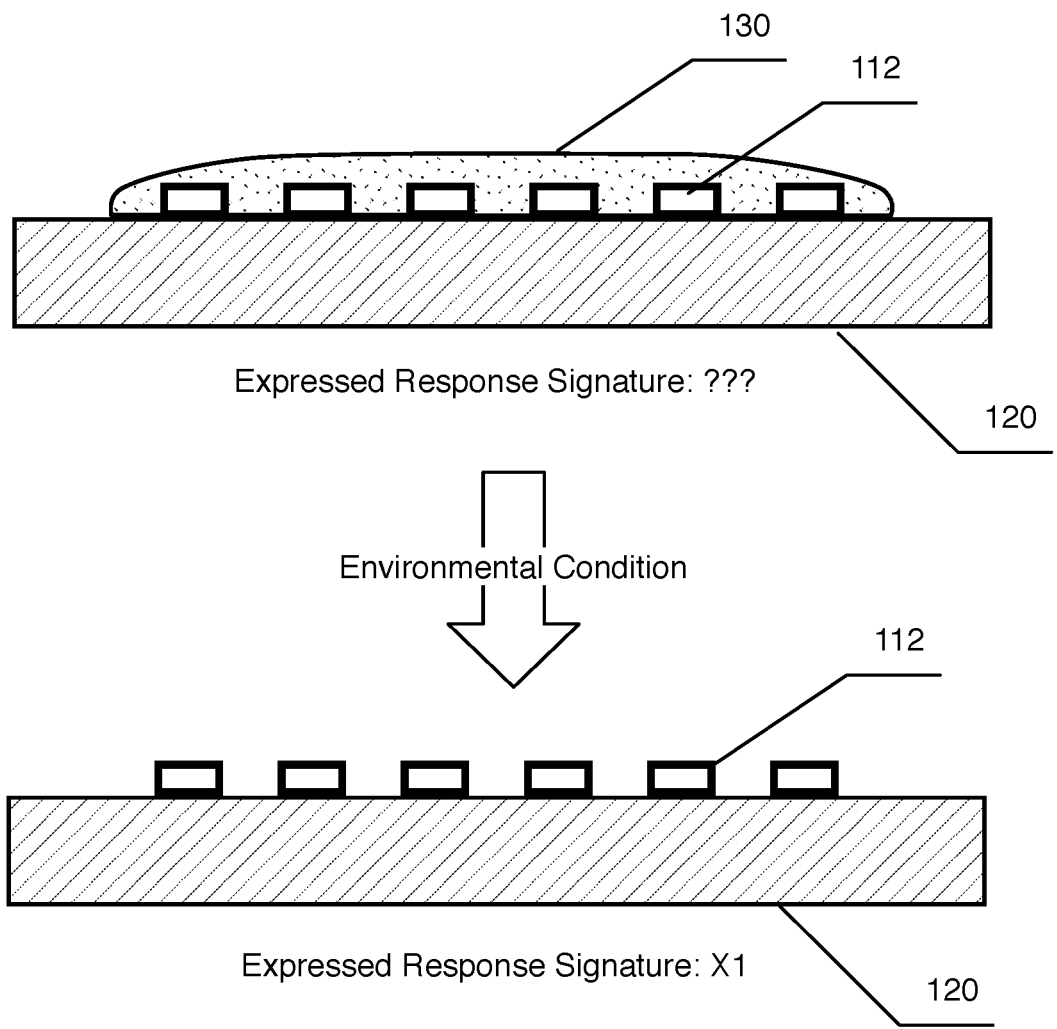

Other variations may utilize other reactive components integrated with the reflector element 110 such as a secondary reactive layer 130. The secondary reactive layer is can be established during a pre or post printing process. The reactive component could be a secondary material layer printed or applied underneath, alongside, or on top of the reflector element 110. The secondary reactive layer 130 can be used to initially shield the reflector element 110 (e.g., a secondary reactive layer 130 covering an antenna structure) or interfere with the reflector element 110 (e.g., a secondary reactive layer 130 printed alongside an antenna structure used to alter the response signature) prior to the secondary reactive layer 130 reacting to the environmental condition as shown in FIGS. 8 and 9. A shielding or interference secondary reactive layer 130 may make the reflector element 110 radio transparent or may alternatively alter the response signature. The secondary reactive layer 130 may similarly alter its properties, erode, dissipate, or otherwise affect change to the reflector element 110. In some variations, the secondary reactive layer 130 may provide structural support and so the reaction to the environmental condition can cause the reactive secondary layer 130 to alter the physical structure of the reflector element 110. For example, a base reactive secondary layer 130 may erode causing parts or all of an antenna structure to be deteriorated.

A reflector site can be configured to act in different activation cycles. The reflector sites could be configured as an activating reflector site, a deactivating reflector site, or a multi-state reflector site. A reflector site may be configured to be destructive in that the reflector site is only usable one time. A reflector site may alternatively be reusable. A reusable reflector site may be able to reset (i.e., "toggle") to a previous state based on the environmental conditions. For example, allowing a base substrate to dry can reset a fluid detecting reflector site as shown in FIG. 6. The type of configured activation cycle may depend on the particular application. In some cases, it may be beneficial to have high confidence that a condition has not happened and so an initial response signature may be desired (e.g., a deactivating configuration). In some cases, it may be beneficial to have high confidence when a condition has happened and a response signature may be desired (e.g., an activating configuration). In other cases, the usage scenario may benefit from having a discernible indicator of different states (e.g., a multi-state configuration).

An activating reflector site is configured to transition to a revealed identifiable interrogation response signature that is expressed in response to and generally after an environmental condition. The activating reflector transitions when a reactive element of the structure element (e.g., a reactive portion of an antenna structure, a reactive base substrate, or a reactive secondary layer) responds to an environmental trigger. Initially, an activating reflector site may generate an inactive response as shown in FIGS. 8 and 9. An inactive response may have no set discernible identifiable response signature or may even be radio transparent.

Figure 10:
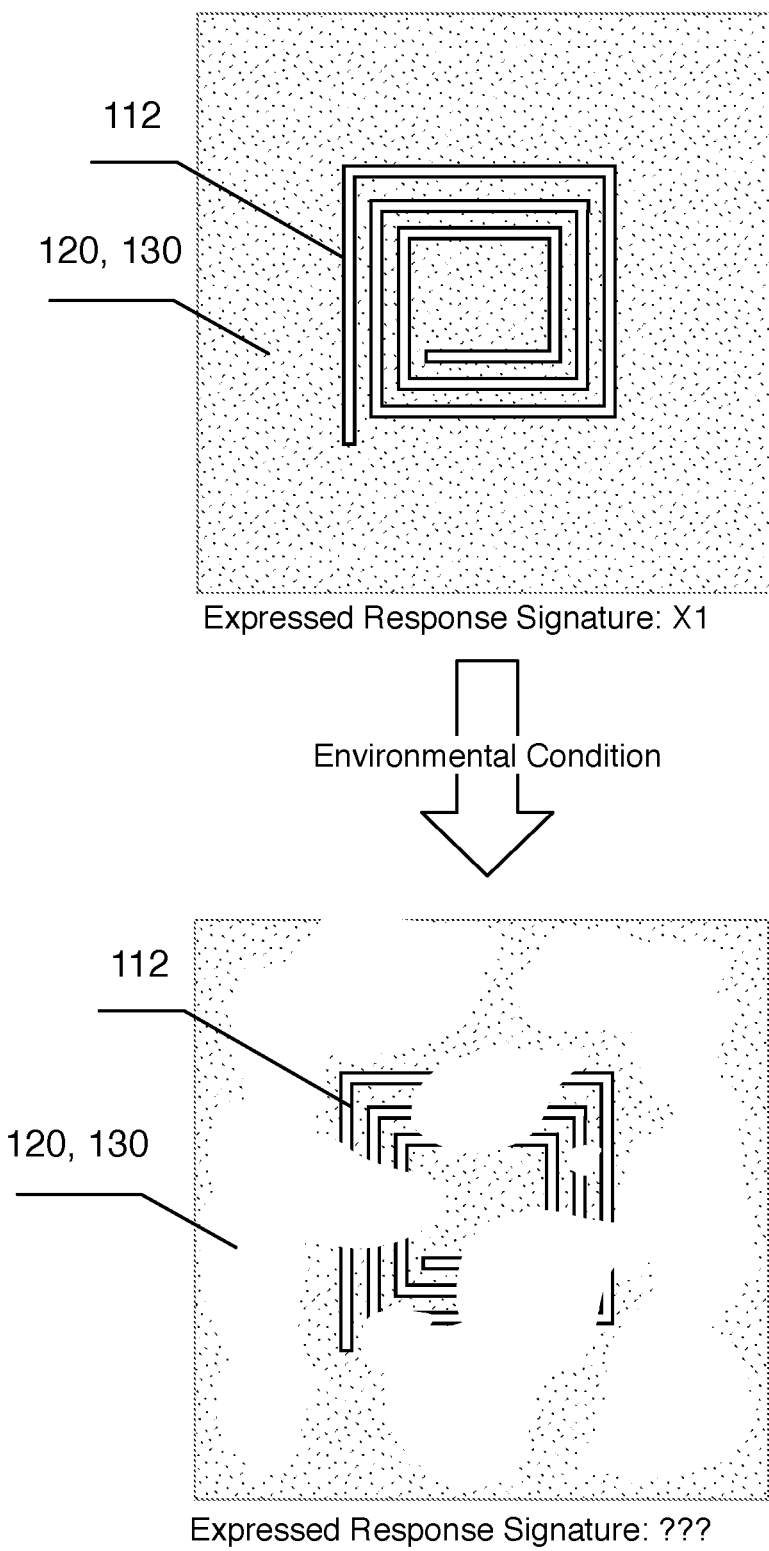
FIGS. 10 and 11 are schematic representations of a transition between response signature states of a deactivating reflector element with a destructively reactive secondary base layer.
Figure 11:
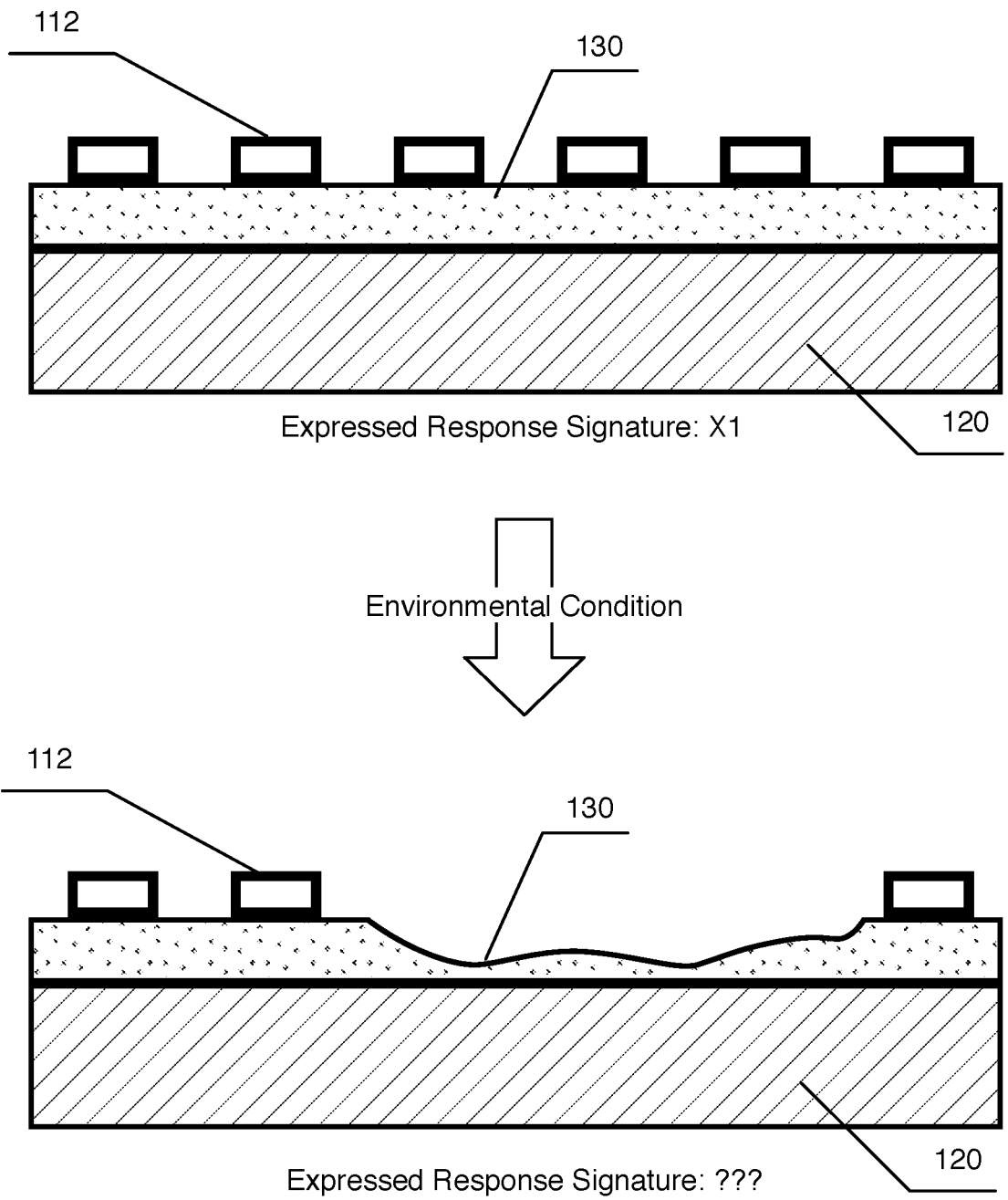

A deactivating reflector site is configured to initially generate an identifiable response signature. The identifiable response signature is then disrupted, or prevented from being expressed as a response to an environmental condition. In one variation, the disruption of the initial response signature can be a destructive transition wherein the reflector element does not naturally regain the initial response signature. After or during the environmental condition, the deactivating reflector site preferably generates an inactive response. As shown in FIG. 10, a reactive base substrate 120 may destructively break apart the antenna structure 110 when a trigger substance is encountered.

Figure 12:
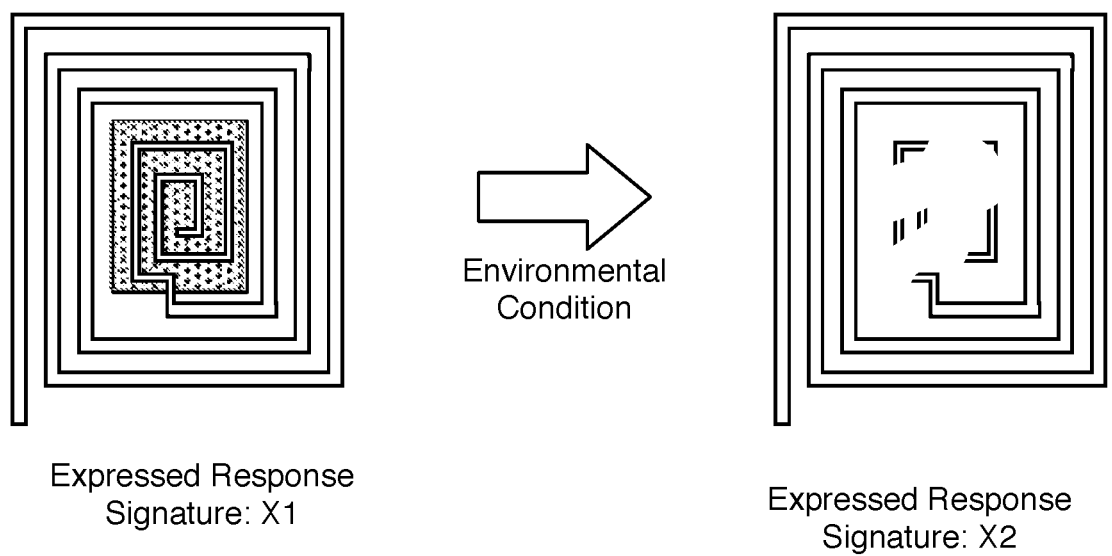
FIG. 12 is a schematic representation of a transition between two identifying response signatures of a two state reflector element.
Figure 13:
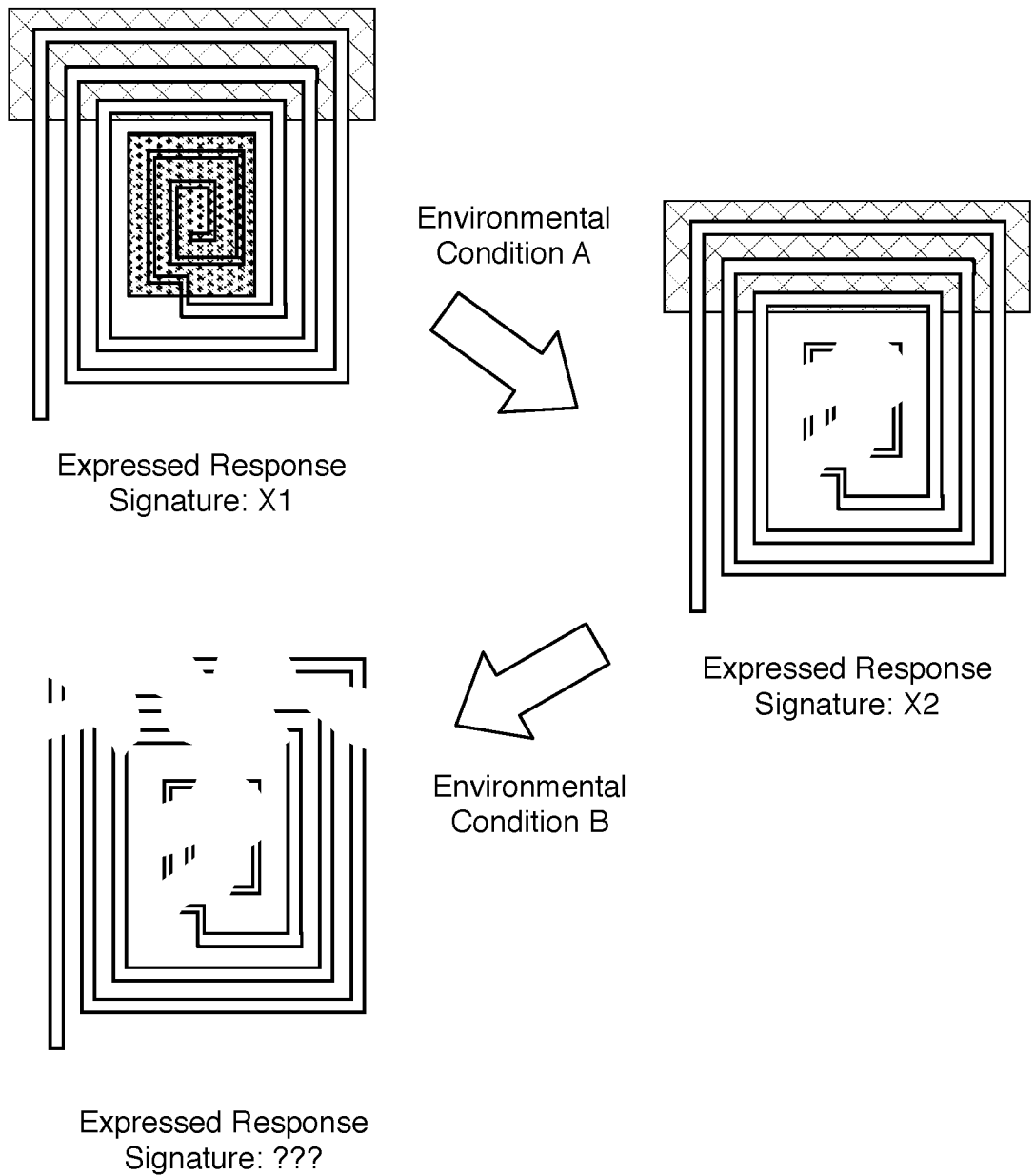
FIG. 13 is a schematic representation of a transition between three identifying response signature states of a reflector element.

A multi-state reflector could transition between a first identifiable interrogation response signature and at least a second identifiable interrogation response signature. A toggling version of a multi-state reflector could enable a reflector site to switch between at least two remotely detectable states. A destructive multi-state reflector may sequentially go through at least two remotely detectable states before the multi-state reflector reaches a terminal final state. In one implementation, an antenna structure has two subsections wherein one subsection is perturbed in response to an environmental condition as shown in FIG. 12. A multi-state reflector could additionally include more than two stages as shown in FIG. 13.

Within a set of reflector elements, one or a subset of reflector elements 110 is preferably identifiable by having a unique electromagnetic or magnetic signal response to that of the other reflector elements 110 of the structure element 100. The combined arrangement of reflector elements 110 may additionally be identifiable from reflector elements 110 from a plurality of different structure element 100s.

The system can be used with a single reflector element 110. The system may alternatively include a set of reflector elements 110 used within a structure element 100. The set of reflector elements 110 preferably includes at least two subsets of reflector elements 110 that are uniquely identifiable for a particular structure element 100. The set of reflector elements 110 can be used to monitor environmental conditions at different points of the structure element 100 and/or to monitor different environmental conditions on the structure element 100. Each reflector element 110 of the set is preferably physically configured to express at least one identifiable response signature depending on the environmental substance condition experienced at that reflector element wherein the identifiable response signature can be distinguished from at least a second reflector element 110 of the set.

Figure 14:
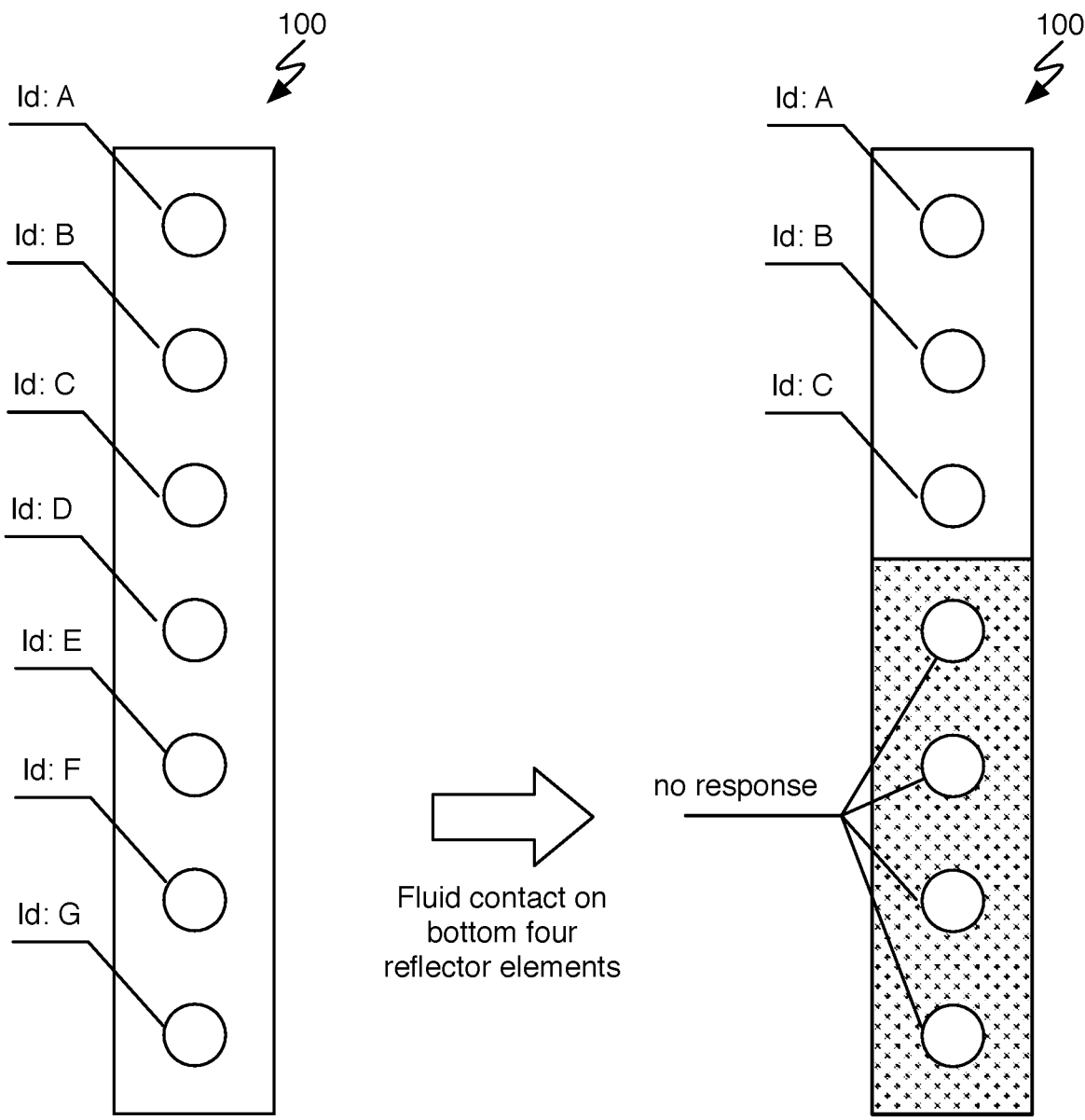
FIG. 14 is a schematic representation of a set of reflector elements responding to environmental conditions.
Figure 15:
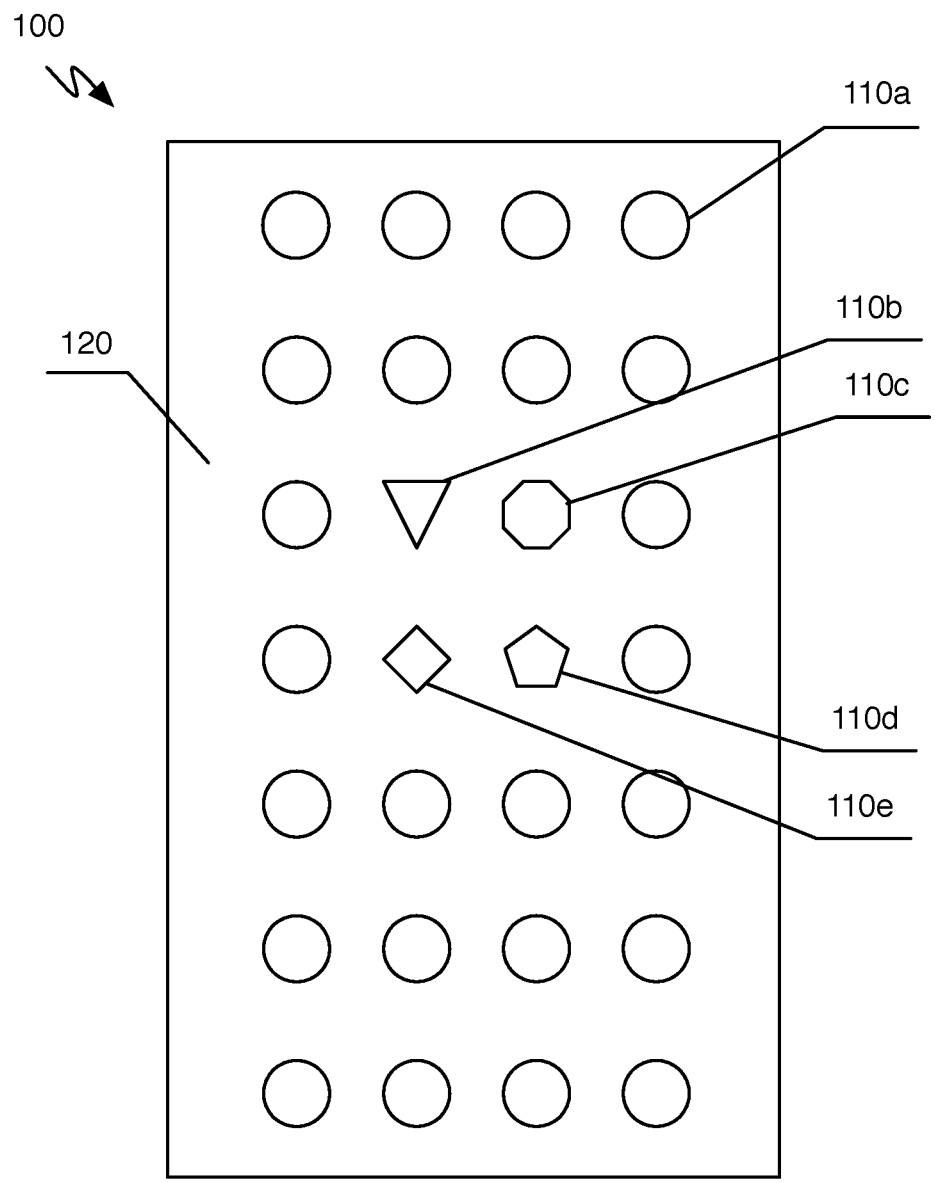
FIG. 15 is a schematic representation of multiple types of reflector elements used on one structure element.

The identifying interrogation response signature of a first reflector 110 can preferably be distinguished from the identifying interrogation response signature of a second reflector 110. The identifying interrogation response signature of a reflector element 110 can be mapped to a position within the structure element 100. The identifier to position mapping can be stored remotely in an application or network accessible database. Alternatively, the identifier to position mapping may be based on a predefined schema for encoding the position information in the identifier. The position mapping may be used in monitoring or predicting environmental conditions. For example, the linear array of reflector elements shown in FIG. 14 can be used to indicate the level at which a substance has been absorbed and deactivated the response signals of the corresponding reflector elements. has been Additionally or alternatively, the identifying interrogation response signature of a reflector element 110 can be mapped to a type of reflector element 110 which can be used to determine the indicated environmental condition. More specifically, a first subset of reflector elements may be reactive to a first environmental substance condition and a second subset of reflector elements may be reactive to a second environmental condition. For example, a first type of reflector element 110 may be used to detect fluid presence while a second type of reflector element 110 can be used to indicate presence or a particular chemical. As shown in FIG. 15, four different reflector elements (110b, 110c, 110d, 110e) may be included in the set to detect four different substances and a fifth type of reflector elements 110a can be used to indicate fluid saturation.

Figure 17:
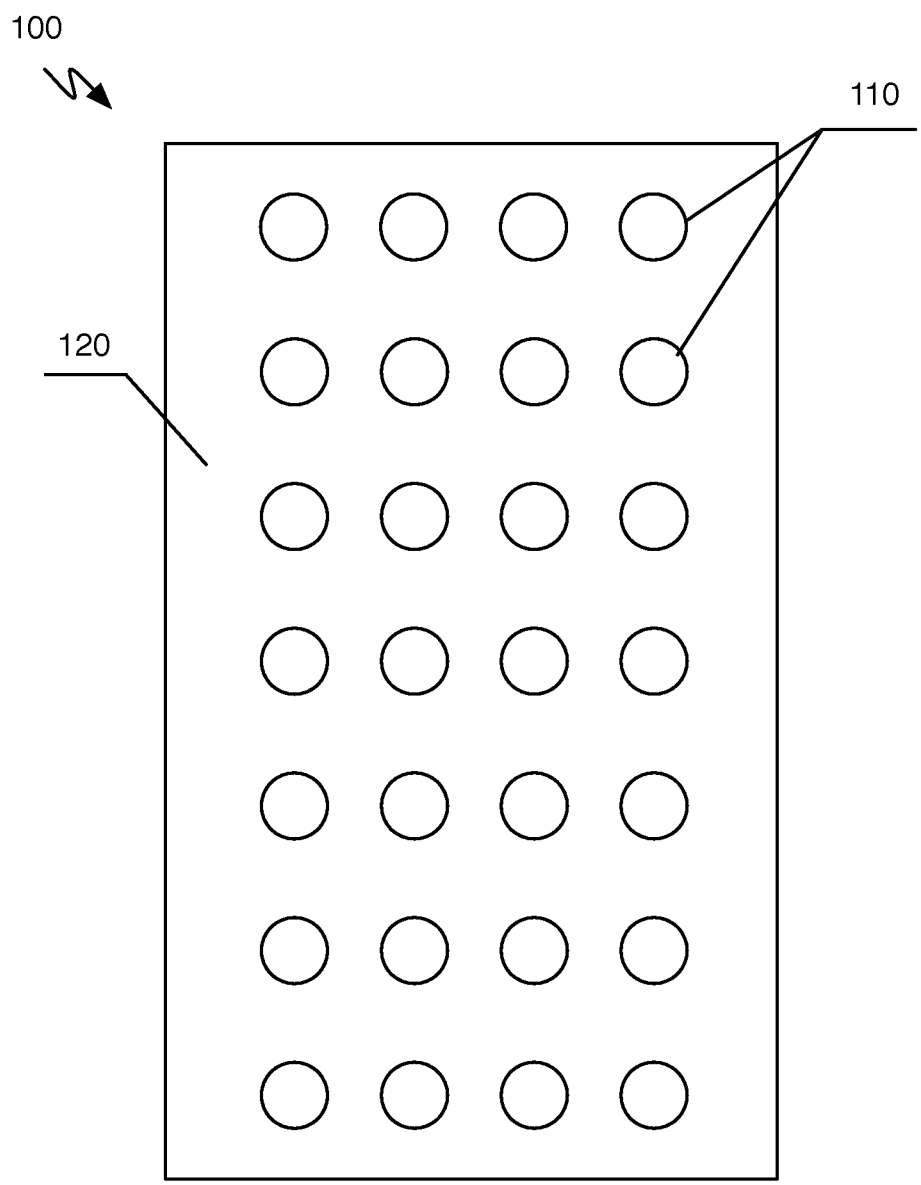
FIG. 17 is a schematic representation of an exemplary arrangement of reflector elements along two dimensions.
Figure 18:
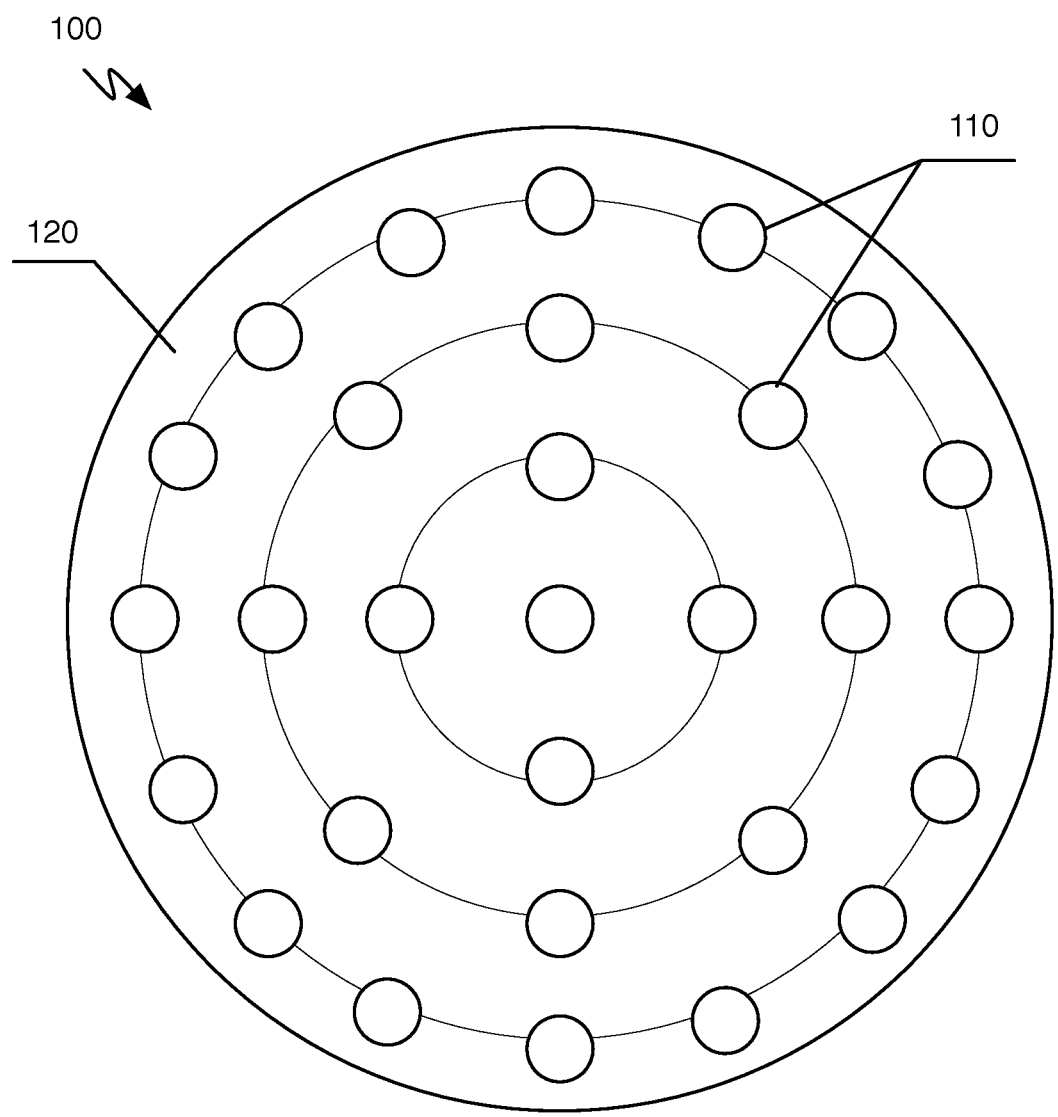
FIG. 18 is a schematic representation of an exemplary arrangement of reflector elements along two dimensions in a radial pattern.

Preferably, the set of reflector elements 110 are printed with conductive ink on the base substrate 120. The set of reflector elements 110 are preferably printed in a distributed pattern, wherein the configured response signature a reflector element 110 corresponds to its printed location within the structure element 100. The pattern of reflector elements 110 is preferably customized for the particular use case. When the structure element 100 is an absorbent device, the set of reflector elements are preferably printed in a pattern across a dryness inspection zone. In a container structure element 100, the set of reflector elements may be distributed linearly along the length of an inner wall of the container so that the contents level may be remotely monitored. In one variation, the set of reflector elements 110 are printed across a two-dimensional surface of the base substrate 110 to provide information along two dimensions, as shown in FIG. 17. In a related variation, the set of reflector elements 110 can be arranged in a radial pattern, as shown in FIG. 18. When used within an absorption structure element 100, a radial pattern may be used to show dryness information around a central zone. The radial pattern preferably has the central zone located at a likely initial region of fluid absorption, with a series of outer zones showing outward leaking. Additionally or alternatively, the set of reflector elements 110 can be printed at different layers or depths within the base substrate 110, which functions to enable reflector elements 110 to be stacked or layered.

Figure 20:
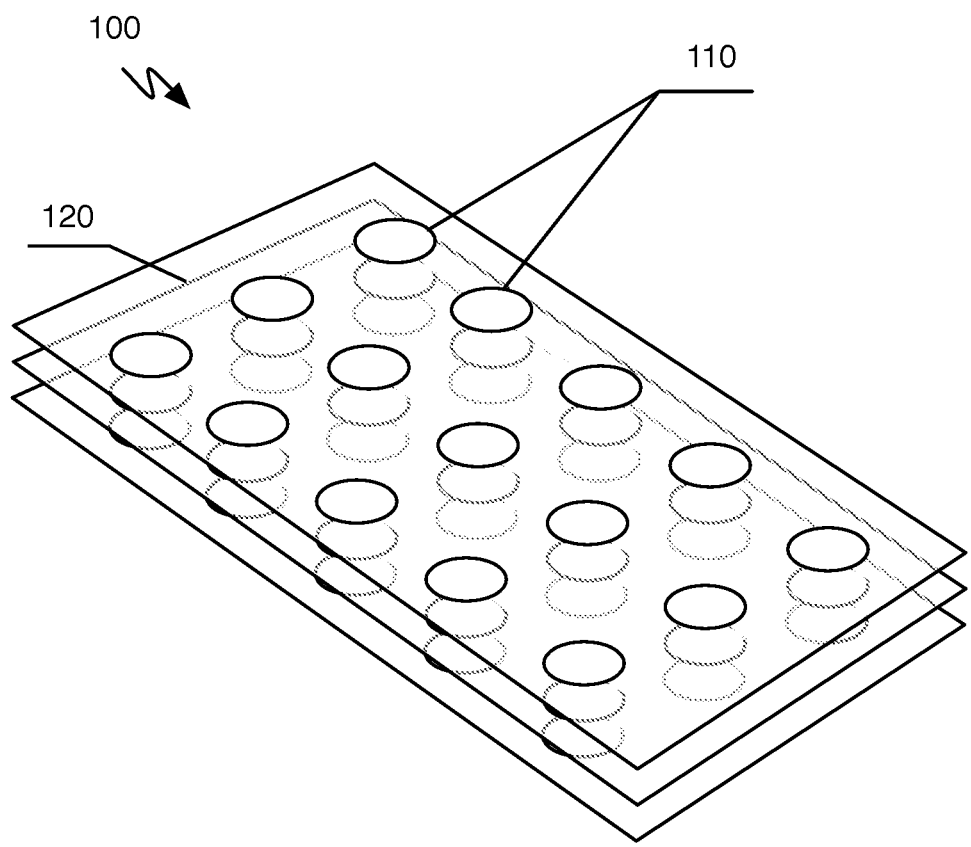
FIG. 20 is a schematic representation of an exemplary arrangement of reflector elements distributed across multiple layers in the material of a structure element.
Figure 21:
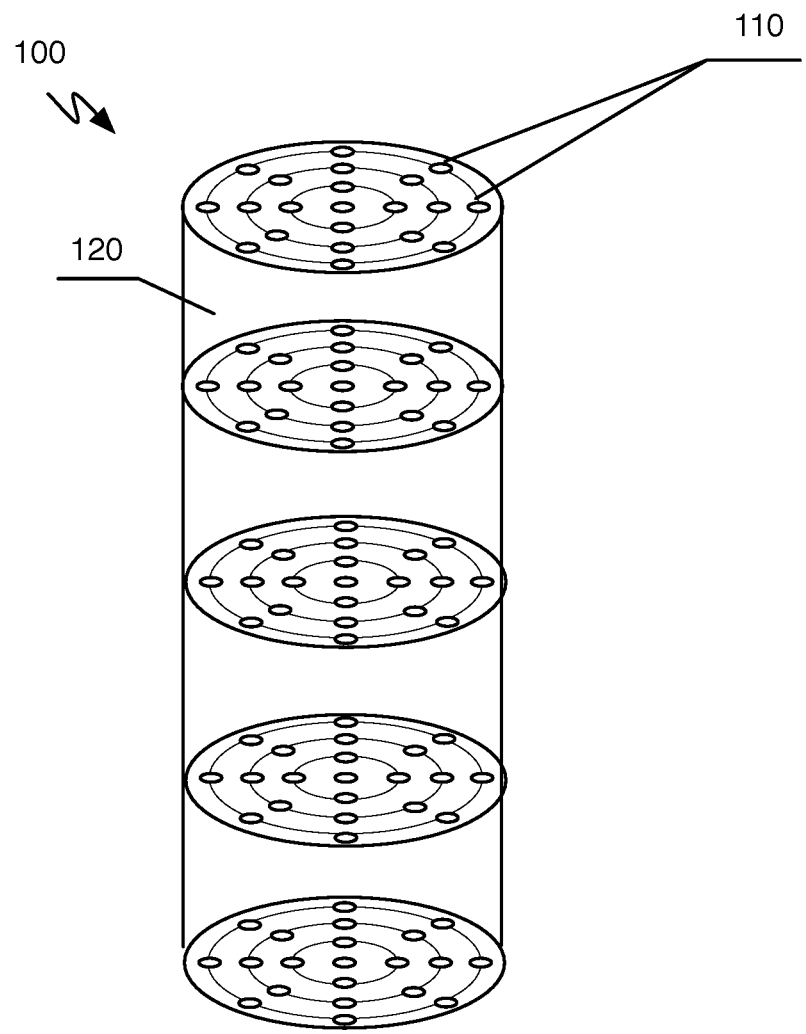
FIG. 21 is a schematic representation with cross sectional highlights of an exemplary arrangement of reflector elements in a tampon.

In yet another variation, the reflector elements 110 can be arranged in three dimensions, which may function to provide environmental condition information across a surface as well as within a substrate. For example, there could be multiple layers of two-dimensional arrays of reflector elements 110. Reflector elements 110 in a first layer may be offset from a reflector element 110 in a second layer as shown in FIG. 20. The reflector elements 110 may alternatively be stacked. As shown in FIG. 21, sets of radially arranged reflector elements 110 may be distributed at different points along the length of a tampon, which can function to provide dryness information in three dimensions.

The pattern of reflector elements 110 may alternatively be customized to the particular structure element 100, random, or with any suitable pattern.

In another variation, the pattern of reflector elements 110 could be dynamically specified for an individual structure element 100. For example, a doctor or nurse may be able to take a picture of a wound and then define where the central area of the wound is located. A pattern of reflector elements 110 radiating outward from the defined wound area can be produced for a customized bandage.

Additionally, two different structure elements 100 can have uniquely identifiable sets of reflector elements 110. Preferably the two different structure elements 100 have distinct sets of identifiable reflector elements 110, which function to prevent interference between the reflector elements 110 of the two structure element 100s. For example, the system may be designed to allow two individuals wearing structure element 100s of the system to monitor their respective dryness state without accidentally reading the signals of the nearby structure element 100. Furthermore, such uniqueness between different instances of the structure element 100 can function to preserve privacy so that others cannot easily interrogate the state of the structure element 100.

The system can additionally include an instance synchronizing mechanism, which functions to register the expected reflector element 110 responses with a monitor device. The synchronizing mechanism can be a uniquely coded package of one or more structure element 100s. The uniquely coded package can use a QR code, a pin code, an RFID, or any suitable identifying mechanism. In one variation, a packaging identifier is associated with a set of structure element 100s. During the initial use of a structure element 100, the user may scan or input the identity of the structure element 100. Alternatively, a packaging code can be set for a user account during purchase of one or more packages of the product. For example, a user may setup a subscription to a feminine hygiene product of the system. Each time before delivery, the online marketplace will associate the identifier of the packaging with the user account. When the user uses her application, the application automatically knows what identifiable reflector elements 110 to expect.

Figure 16:
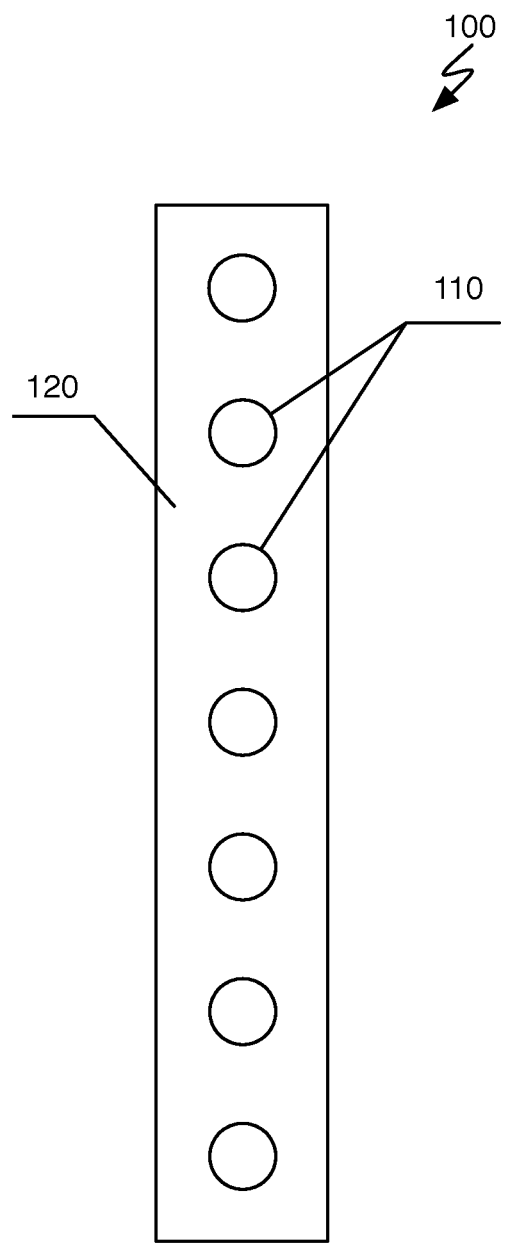
FIG. 16 is a schematic representation of an exemplary arrangement of reflector elements along one axis.

When used within an absorption device, the system can be applied to individually detect the dryness state of each reflector element 110. In one variation, a subset of the reflector elements 110 provides dryness information of a first zone (e.g., initial leaking) and at least a second subset of reflector elements 110 provides dryness information of a second zone (e.g., border of absorption area). The reflector elements 110 are preferably arranged in a pattern on the structure element 100. In one variation, the set of reflector elements 110 are arranged along one axis in a linear pattern, as shown in FIG. 16. The one-dimensional arrangement can show dryness information along one dimension.

The reflector elements 110 can be printed on the contact surface of the structure element 100. In the absorption device variation, the contact surface is the surface in contact with the body. The set of reflector elements 110 are preferably printed in a distributed pattern across the absorbent region of the structure element 100. Preferably, the reflector elements 110 are printed on an inner layer of an absorbent or nonabsorbent material, which functions to enable dryness state detection after fluid has been wicked away from the contact surface. The reflector elements 110 may alternatively be printed on the outer layer of a contact surface or in any suitable inner layer. In one variation, a material layer of the absorption device may cover the reflector elements 110, which may function as a protective layer while still detecting the dryness state at substantially the contact surface. In another variation, one or more of the reflector elements 110 may be embedded within structure element 100. For example, the reflector element 110 can be embedded within the absorbent material of the structure element 100, which can function to detect dryness state of the absorbent material at an inner layer rather than the contact surface. In yet another variation, the reflector elements 110 can be distributed in different layers or depth positions in the structure element 100. As shown in FIG. 21, sets of spatially arranged reflector elements 110 may be distributed at different points along the length of an absorbent form, which can function provide dryness information in three dimensions. In one exemplary implementation, the pattern of reflector elements 110 is distributed across a sanitary napkin with radial distribution of reflector elements 110. The radial distribution of reflector elements 110 includes at least a subset of reflector elements 110 forming an outer border of dryness detection. The subset of reflector elements 110 is preferably placed around a defined border of the absorbent pad, which functions to enable a final warning before eminent leaking occurs. In an alternative variation, the subset of reflector elements 110 can be outside of the absorbent area of the sanitary pad such that an alert can also be made when leaking has occurred. Preferably such a leaking alert is preceded by warnings triggered as a result in the change of the dryness state of the inner reflector elements 110.

The monitor device of the preferred embodiment functions as a remote device that provides monitoring and status information of the structure element 100. The monitor device preferably includes communicative access to a transmitter and receiver unit 210, a control unit 220, and optionally a user interface unit 230. The monitor device 200 is preferably an application operable on a computing device. The computing device can be a smart phone, a tablet, a personal computer, a wearable computer (e.g., watch, ring, bracelet, etc.), or any suitable device. In an alternative embodiment, the monitor device 200 can be a dedicated device with additional components (e.g., battery, processor, user input and output interface elements and the like) used in monitoring the structure element 100. The monitor device 200 is preferably adaptable to being brought into close proximity of the structure unity while in use. The monitor device 200 may be stored in the pocket of a user, clipped on a belt or positioned in any suitable manner. The monitor device 200 may alternatively be physically positioned near the structure element 100 for each scan. For example, a watch or ring may enable the user to easily wave their hand near the structure element 100. In another variation, the system could be operable with multiple monitor devices 200 where a structure element may be scanned by one of a set of different monitor devices 200.

In one variation, operative components of the monitor device 200 can be distributed between distinct devices. For example, a dedicated interrogator device can contain the transmitter and receiver unit 210, a communication mechanism, and/or other suitable components. The dedicated interrogator device preferably inspects the dryness state of the structure element 100 through use of the transmitter and receiver unit 210. The collected information can then be relayed back to a secondary device. The secondary device is preferably a native application running on a smart phone, tablet, or wearable computing device, but may be any suitable secondary computing device. The dedicated interrogator device can communicate with the secondary device over Bluetooth, a wired connection, Wi-Fi, or any suitable communication channel. Distributing the monitor device 200 between at least two devices can function to enable a standardized transmitter and receiver unit 210 to be designed so as to work across a wider variety of devices while still allowing use of a personal computing device when the user interacts with the application.

The transmitter and receiver unit 210 of the preferred embodiment functions to wirelessly interrogate the reflector elements 110 to determine the environmental condition of the structure element 100. The transmitter and receiver unit 210 preferably transmits an electromagnetic signal and more preferably a radio frequency signal. The transmitter and receiver unit 210 can operate as an electromagnetic backscatter interrogator. Any suitable frequency range of the electromagnetic spectrum may be used. In one implementation, the transmitter and receiver unit 210 scans across a range of frequencies to identify resonant responses from a reflector element 110. The transmitter and receiver unit 210 preferably monitors the set of identifiable reflector elements 110. Preferably, the transmitter and receiver unit 210 is pre-configured with the expected identifiers for the set of identifiable reflector elements 110. The pre-configured expected identifiers can be set through the instance synchronizing mechanism (e.g., scanning a QR code of a structure element 100 product).

The control unit 220 functions to be communicatively coupled to the transmitter and receiver unit 210 and the transmitter and receiver unit 210. The control unit 220 may manage the operation of the transmitter and receiver unit 210. The control unit 220 can direct the transmission signal. The control unit 220 may additionally interpret received signals. The transmission signal may be modulated according to feedback of the received signals. The control unit 220 can additionally apply a higher-level algorithm to interpret the collective environmental condition information. For example, the dryness state of multiple reflector elements 110 of an absorption device may be used to determine the dryness state of the structure element 100.

In one absorption device variation, the control unit 220 can include a capacity estimate output. The capacity estimate in one implementation can be a time until expected full usage. The capacity estimate may alternatively be a percentage of usage. For example, one hundred percent may indicate that the structure element 100 is brand new and zero percent may indicate the structure element 100 should be changed. In another variation, the control unit 220 may supply more detailed information such as a condition map of the structure element 100 showing measured and/or predicted dryness state. The control unit 220 may generate any suitable output or data.

The monitor system can additionally include a transmitter positioning system 240, which functions to facilitate tracking the position of the monitor system relative to a structure element 100. The transmitter positioning system can be an inertial measurement unit. An inertial measurement unit can include an accelerometer, a gyroscope, a camera, and/or any suitable detector of translational motion. The transmitter positioning system 240 can be operative in cooperation with the control unit 220 to modulate the transmission signal to appropriately target the structure element 100. The transmitter positioning system 240 is preferably calibrated with some known or expected position relative to the targeted structural element 100. The displacement from that calibration point can be tracked so that the current relative position can be calculated.

The remote monitor device 200 may additionally include a user interface unit 230, which functions to be an interface through which a user can provide input and receive information. The transmitter and receiver unit 210 is preferably part of a native application. The native application can include an account system and be connected to a web platform. The history of usage by a particular user can additionally be used in the control of the transmitter and receiver unit 210 or in the generation of notifications. The transmitter and receiver unit 210 additionally manages information display, alerts, notifications, and/or other forms of informing a user. The user interface can additionally include a user interface to facilitate the instance synchronizing mechanism such as a QR code scanner or pin input. The transmitter and receiver unit 210 is designed for individual use in one application, but can alternatively be designed for multiple users. For example, a single application can be designed for monitoring multiple patients in a hospital.

2. Method for Monitoring Environmental Status

Figure 22:
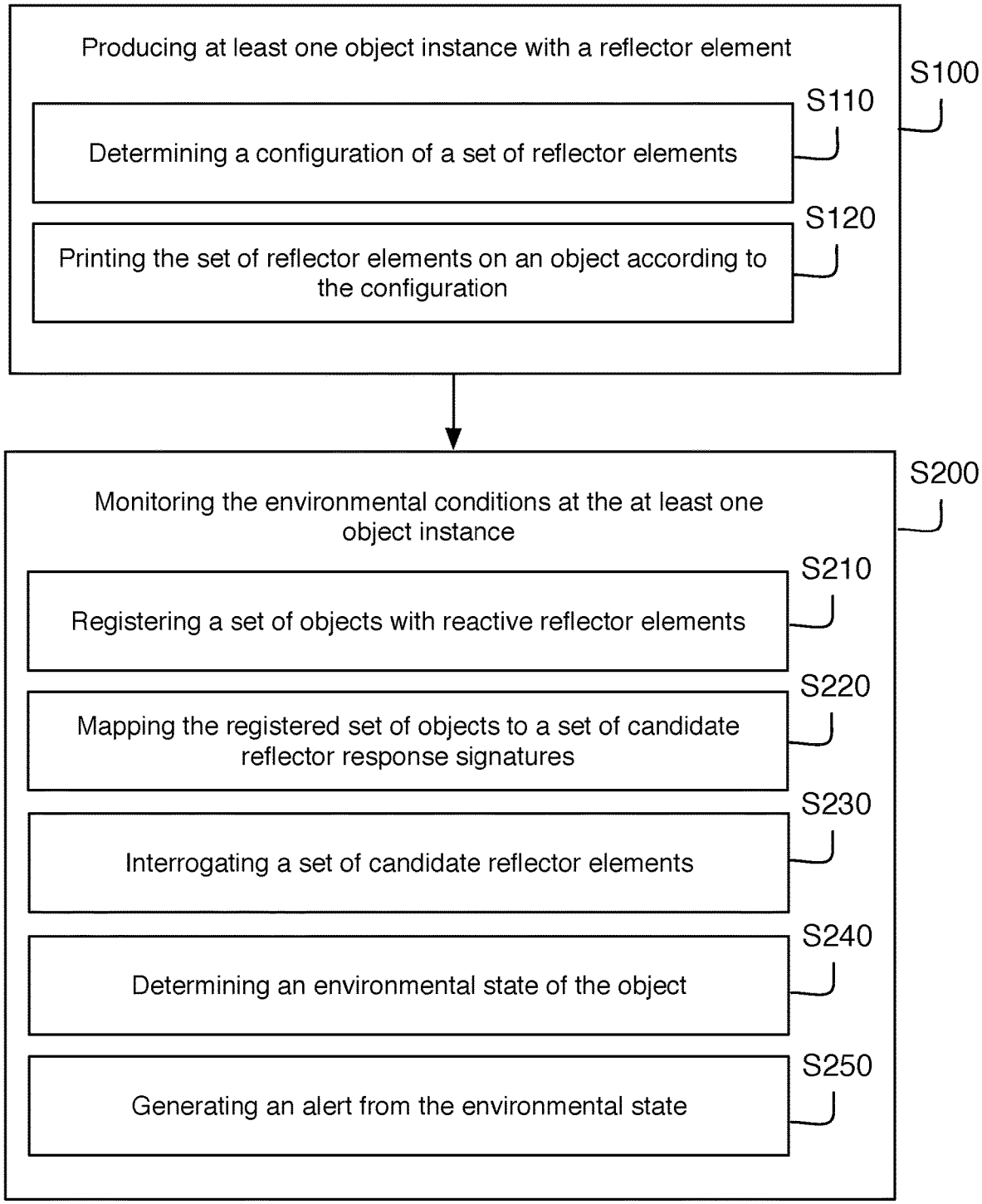
FIG. 22 is a flowchart representation of a method of a preferred embodiment.

As shown in FIG. 22 a method for monitoring environmental status through a reactive reflector of a preferred embodiment can include producing at least one object instance with a reflector element S100 and monitoring the environmental conditions at the at least one object instance S200. Producing the at least one object instance with a reflector element S100 can include determining a configuration of a set of reflector elements S110 and printing the set of reflector elements on an object according to the configuration S120. Monitoring the environmental conditions at the at least one object instance S200 can include registering a set of objects with reactive reflector elements S210, mapping the registered set of objects to a set of candidate reflector response signatures S220, interrogating a set of candidate reflector elements S230, and determining an environmental state of the object S240. The method functions to enable the environmental status of an object to be remotely determined. The method can additionally include generating an alert from the environmental state S250, which functions to enable notifications to be delivered at appropriate times. The method is preferably used for enhanced absorption devices, wherein an absorption device may be a feminine hygiene product such as a sanitary napkin or a tampon, a bandage, a diaper, or any suitable absorption device. The monitored environmental status can be dryness state of the enhanced absorption device. The enhanced absorption devices preferably include an integrated set of identifiable reflector elements as described above. The method may alternatively be used in objects used for chemical or substance detection, container contents monitoring, seal disruption detection, and/or any suitable application. Herein, absorption devices will be used as the primary example, but any suitable application may be used and the method is not limited to just absorption device applications.

The method is preferably implemented by a system substantially similar to the one described above, but any suitable system may alternatively be used. The object of the method is preferably a structure element as described above.

Block S110, which includes determining the configuration of a set of reflector elements, functions to setup how a set of reflector elements is to be produced. Determining the configuration can include determining the number of reflector elements, placement of reflector elements, the type of reflector elements, and/or the response signature mappings for the set of reflector elements.

The method may be implemented using a single reflector element. Alternatively, the set of reflector elements can include more than one reflector element. Multiple reflector elements are preferably used to detect multiple types of environmental conditions or to detect environmental conditions at multiple locations of the object or environment. The type of a reflector element can impact what type of environmental condition and the particular properties to which a reflector element may respond.

As a first possible variation, a reflector element can be configured to detect different classes of environmental conditions. In one variation, the environmental condition is related to the dryness state at the location of the reflector element (e.g., the amount of fluid saturated at the reflector element). In another variation, the environmental condition is based on a chemical reaction between a reactive element of a reflector element and a trigger substance. For example, the reflector element could utilize materials and/or structures that promote a reaction to the presence of a particular biochemical, which may be used to indicate signs of blood chemistry, cancer, pathogens, or other bio-related signals. The exact conditions and sensitivity may be set which is then mapped to particular material composition and/or structural design of a reflector element. For example, a first reflector element may be used to detect presence of a first reagent. A shielding secondary reactive layer can be configured to cover an antenna structure, and the secondary reactive layer degrades based on the presence of the first reagent until the response signal of an antenna of the reflector element is exposed. The thickness of the shielding secondary reactive layer can be set based on the amount of exposure before the reflector element is activated.

As a second possible variation, the reflector element can be configured for a particular activation cycle. The configured design for a reflector site can be altered based on if the activation cycle of the reflector site should be an activating configuration, a deactivating configuration, or a multi-state configuration.

The location of the reflector elements can additionally be configurable. The positioning of multiple reflector elements can define where the environmental conditions are sensed within the object. The positioning can be two-dimensional across some surface or layer, but the positioning could alternatively be three-dimensional where reflector elements are positioned within the object. In one variation, the exact location of a reflector element can be set. In another variation, a user may indicate main sources of a monitored substance, which is then used to automatically generate a positional array of reflector elements to track the trajectory of that substance from those sources. For example, a doctor can create a customized bandage with blood detection along an incision path. Specifying this incision path can configure a set of reflector elements to be printed on a bandage radiating outward from the bandage area bordering the incision path.

Additionally, the various reflector elements are configured with particular identifying response signatures. Each reflector element may be configured to have a unique identifying response signature. Alternatively, subsets of reflector elements may be configured with identifying response signatures that are unique to that subset of reflector elements.

Furthermore, when multiple instances of an object will be used in close proximity, it may be desired to distinguish between the two object instances. The reflector elements could be uniquely identifiable for that one object but also across a set of objects. Herein, unique may refer to globally unique, but more preferably refers to the state of being substantially unique. Substantial uniqueness can enable identification of reflector elements from a limited set of reflector elements (e.g., between 100 reflector elements) and/or objects (e.g., between 50 object instances). For example, a reflector element may be assigned a response signature selected out of one thousand possible identifying response signatures.

Block S120, which includes printing the set of reflector elements on an object according to the configuration, functions to apply the desired properties for detecting environmental conditions to the production of one or more reflector elements. The object could be any suitable object. In one instance, a surface of the object can act as a substrate on which the reflector element is printed. Alternatively, a base substrate may be applied to the object.

In a basic production process, the printed material and the pattern of printing can create a site that produces an identifying response signature based on an environmental condition. The pattern is preferably a two-dimensional antenna coil pattern but any suitable pattern may be used. The pattern of the antenna structure preferably promotes some resonance frequency response to an interrogating electromagnetic transmission and generates a detectable backscatter pattern as a result. The ink used to print is preferably conductive ink. The ink may additionally be reactive.

As one variation, the base substrate may provide the reactive mechanism used in altering the response signature of the reflector element. That reactive mechanism could be through a physical or chemical property. As an example of a physical property, the base substrate may absorb a fluid and as a result alter the response signature of the reflector element. As an example of a physical property, the base substrate may undergo a chemical reaction. In one variation, the chemical reaction could alter the impedance properties and as a result alter the response signature of the reflector element. In another variation, the chemical reaction could cause a structural deterioration of a portion of the reflector element, and as a result alter the response signature of the reflector element. For example, a portion or all of an antenna structure may be disrupted by the dissolving or breakdown of the base substrate.

Alternative manufacturing and production approaches may utilize a secondary reactive layer. The secondary reactive layer could be printed or otherwise applied underneath, alongside, or over the reflector element. Multiple secondary layers may be printed when producing a reflector element. In one variation, a secondary reactive layer is applied as a shielding coating.

When multiple instances of an object are to be used in close proximity, the reflective elements should be distinguishable between different instances. For example, each individual absorption device, package set, order shipment, or subset of absorption devices includes a distinguishable set of identifiable reflector elements. In this variation, a measured signal or signals from a first absorption device can be distinguished from a measured signal or signals from a second absorption device. This absorption device distinction can function to prevent the occurrence of interference from multiple absorption devices in close proximity. Furthermore, the pairing of a particular absorption device to a monitoring device can improve privacy by preventing others from reading the device.

In a preferred implementation, a user will employ an RF-enabled device such as a smart phone, smart watch, or other personal computing device to interact and monitor the status of an absorption device. A standalone or distributed monitoring device solution can alternatively be used. As an exemplary use-case, a woman could buy a package of enhanced sanitary pads. She then can use a scanning application on her phone to scan or enter a code printed on the sanitary napkin package. This registration process will identify what identifiable reflector elements the scanning application can expect during interrogation and where each will be located on or in the product. After applying the sanitary napkin, she can complete an initialization step where she does an initial interrogation to calibrate the system. By placing the phone in her pocket or reasonably nearby, the scanning application can periodically monitor the absorption device. The signals from the absorption device can then be used to determine the overall state of the absorption device. Various notifications can be delivered to the woman including when menstruation begins, an estimate on when the absorption device should be changed, when leaking has occurred, and other suitable information.

Block S210, which includes registering a set of objects with reactive reflector elements, functions to identify the particular instance. The registering of a set of objects can include pairing a monitoring device to one particular object instance or to a set of object instances. Pairing to a set of object instances can be useful if a user purchases a package with multiple object instances—the user can be alleviated for registering each object instance individually. In some cases, the method may be performed without registering. In some use cases, there may not be possibly interfering reflector elements.

In the absorption device implementation, registering a set of absorption devices synchronizes a monitoring device with the absorption device or devices that may be monitored. Registering preferably includes the transfer of a device or package identifier with that of the monitoring device. The transfer can be facilitated through scanning of a QR code, bar code, or other machine-readable code. Similarly, an alphanumeric code printed on the absorption device can be entered in the monitoring device. In another variation, the registration of a set of absorption devices can occur as part of an operational workflow when supplying a user with an ordered package of absorption devices. For example, a user can subscribe to the absorption devices in association with a user account. Prior to sending the package of absorption devices, the identity of the package can be scanned so as to register the absorption devices for the user account prior to delivery. As a result the end user can begin use of the absorption device without personally registering the absorption device with the monitoring device.

Registering a set of absorption devices can include registering an individual absorption device. For example, each absorption device may have a code printed on the packaging or directly on the product. Registering a set of absorption devices may additionally or alternatively include registering multiple absorption devices. Multiple absorption devices are preferably packaged together such as a box of ten absorption devices. The absorption device may each have substantially the same set of identifiers for the set of reflector elements. Alternatively, a subset of the absorption devices may have distinct identifiers for the set of reflector elements, wherein two absorption devices in the same box may not interfere.

Block S220, which includes mapping the registered set of objects to a set of candidate reflector response signatures, functions to determine what identifying responses to expect during interrogation. The candidate reflector response signatures can define the set of reflector element identifiers for an absorption device. The absorption device includes a set of reflector elements substantially as described in the system above. The reflector elements can each have an identifier associated with them that is characterized by an antenna structure or some alternative mechanism. A monitoring device preferably has access to a database that maps registration codes to reflector response signatures. The database may be remotely accessible. The monitoring device can call out to a remote server specifying a registration code to query the candidate reflector responses. Alternatively, the database may be locally stored. In another variation, the registration code may follow a protocol so as to specify the expected reflector response signature. Any suitable mapping approach may alternatively be used.

The set of candidate reflector response signatures can be for a single response signature. The set of candidate response signatures may alternatively be for a set of different response signatures, which is preferably used when a registration code is used for a package of multiple absorption devices. The monitor device is preferably not limited to transmitting an interrogation signal for a candidate reflector response of a single absorption device. Multiple absorption devices can be considered during an initialization process. Once an absorption device is identified however, the monitor device can narrow the interrogation process to scan for the specific absorption device. In addition to informing the monitor device as to what reflector element signals to consider, the mapping can specify contextual information for each reflector element identifier. The contextual information preferably includes antenna location information so that the monitor device can determine the state of the absorption device (e.g., leaking occurred near border).

S230, which includes interrogating a set of candidate reflector elements, functions to transmit an electromagnetic signal so as to detect the state of the set of reflector elements. The reflector elements are preferably passive and during initial conditions will have an expected response to an electromagnetic signal transmission. The presence of liquid near or on the reflector element will alter the reflector element response. A transmitter and receiver unit preferably reads the electromagnetic backscatter of a transmitted signal. Interrogation of the set of candidate reflector elements can include detecting backscatter patterns indicative of a reflector element in a dry state. Accordingly, a change in a reflector element can indicate the reflector element is in or entering a non-dry state. The interrogation of the set of candidate reflector elements includes multiple modes.

During an initialization mode, the interrogation can include interrogation for multiple candidate reflector response signatures. A detected reflector response signature of an absorption device can indicate the current object instance of a registered set of possible object instances. Other possible candidate reflector response signatures for other registered object instances may not be considered until re-initialization when beginning use of a new absorption device.

In a tracking mode, the method may additionally include adjusting interrogation of the candidate reflector elements according to relative position of a monitor device and an absorption device. Adjusting interrogation of the candidate reflector elements can include tracking relative position of the monitor device to the absorption device and adjusting a transmitted and/or received electromagnetic response according to the relative position. The orientation and position of the monitor device may alter the expected reflector response. Additionally, the transmission can be modified to better target the absorption device based on current relative position. Tracking of relative position is preferably performed using an inertial measuring unit, which can include an accelerometer, gyroscope, vision system, or any suitable motion/orientation sensing approach. The tracking mode may additionally perform a search mode wherein beam forming, actuation of the transmitter, or other techniques are used to adjust the interrogated region.

Block S240 which includes determining an environmental state of the object, functions to process the interrogation results. For an absorption device, the environmental state is preferably a dryness state. The dryness state is preferably determined from received responses from the set of reflector elements. Determining a dryness state preferably includes determining and tracking the state of each reflector element of an identified absorption device. In one variation, the method can distinguish between substantially dry and non-dry states. In another variation, the signal response of a reflector element may provide an evaluation of dryness. Determining a dryness state of the absorption device additionally includes processing the dryness state of multiple reflector elements as well as contextual information associated with the multiple reflector elements. The contextual information preferably includes location information. The determined dryness state across multiple points in the absorption device allows different state information or predictions to be made for the overall absorption device. This absorption device information can be delivered to a user through block S250, generating an alert from the dryness state. Information can relate to fluid absorbance, fluid flow prediction (e.g., when fluid will leak out of the evaluation area), fluid origin, fluid quantification, fluid distribution, product life prediction, and/or any suitable information.

In other applications, the environmental state may relate to encountered substances, the trajectory of a substance through an environment, or any suitable analysis of the reflector element states.

The method can additionally include applying the method simultaneously across a set of users. This variation may function to apply the method to hospitalization or other care institute environments where multiple absorption devices can be monitored simultaneously. For example, a nursing home could know which patients will need a change.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A system comprising:
    a structure element comprising:
        a base substrate, and
        at least one reflector element integrated with the base substrate, wherein the reflector element is physically configured to have at least one response signature that is expressed based on a substance induced environmental condition; and
    a monitor device that is configured to: wirelessly interrogate the structure element, detect a response signature corresponding to at least the one reflector element, and determine the substance induced environmental condition from the detected response signature.

2. The system of claim 1, wherein the at least one response signature that is discretely expressed based on the substance induced environmental condition is at least partially dependent on a chemical reaction between a material of the structure element and a targeted substance contacted within the environment.

3. The system of claim 2, wherein the targeted substance is a gas.

4. The system of claim 2, wherein the targeted substance is a liquid.

5. The system of claim 1, wherein the reflector element is a multi-state reflector with at least a second response signature that is expressed by the reflector element in response to a second substance induced environmental condition.

6. The system of claim 1, wherein the response signature is an identifiable electromagnetic signal response.

7. The system of claim 1, wherein the response signature is an identifiable magnetic signal response.

8. The system of claim 1, wherein the response signature is discretely expressed based on a chemical reaction with a targeted substance contacted within the environment.

9. The system of claim 1, wherein the reflector element is physically configured in an activating configuration with a revealed response signature that is expressed after a reactive element of the structure element is exposed to the substance induced environmental condition.

10. The system of claim 1, wherein the reflector element is physically configured in a deactivating configuration with an initial response signature that is disruptively altered when the structure element is exposed to the substance induced environmental condition.

11. The system of claim 1, wherein the structure element includes a set of reflector elements that are each physically configured to express at least one identifiable response signature depending on the substance induced environmental condition experienced at that reflector element.

12. The system of claim 11, at least a first subset of reflector elements is reactive to a first substance induced environmental condition and a second subset of reflector elements is reactive to a second substance induced environmental condition.

13. The system of claim 11, wherein the set of reflector elements are distributed across a layer of the base substrate, and wherein the response signature of a reflector element corresponds to a position of the reflector element.

14. The system of claim 11, wherein the set of reflector elements is additionally distributed across a set of different layers of the base substrate.

15. The system of claim 1, wherein a reflector element comprises an antenna structure that is printed with conductive ink, wherein the antenna pattern is configured with an electromagnetic resonance frequency that corresponds to the identifiable response signature of the reflector element.

16. The system of claim 1, wherein the structure element is part of an absorbent device.

17. The system of claim 1, wherein the structure element is a container.

18. The system of claim 1, wherein the structure element is a seal.

19. A method comprising:
    printing a set of reflector elements on a base structure, wherein each reflector element instance has at least one response signature that is expressed based on a substance induced environmental condition at the reflector element instance; and
    monitoring environmental state at the base structure, which comprises:
        at a monitor device, interrogating for a set of candidate reflector signatures;
        detecting a set of detected response signatures corresponding to at least the one reflector element; and
        determining an environmental state of the object from the set of detected response signatures.

20. The method of claim 19, wherein the object is an absorbent device, and wherein determining the environmental state of the object comprises quantifying the fluid absorption capacity of the absorption device according to a set of detected response signatures; and generating an alert from the environmental state.

* * * * *